United States Patent
Ishihara et al.

(10) Patent No.: US 8,981,119 B2
(45) Date of Patent: Mar. 17, 2015

(54) BENZOTHIOPHENE COMPOUND

(71) Applicant: Astellas Pharma Inc., Tokyo (JP)

(72) Inventors: Tsukasa Ishihara, Tokyo (JP);
Kazuhiro Ikegai, Tokyo (JP); Ikumi Kuriwaki, Tokyo (JP); Hiroyuki Hisamichi, Tokyo (JP); Nobuaki Takeshita, Tokyo (JP); Ryuichi Takezawa, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/298,208

(22) Filed: Jun. 6, 2014

(65) Prior Publication Data

US 2014/0364421 A1    Dec. 11, 2014

(30) Foreign Application Priority Data

Jun. 6, 2013    (JP) .................. 2013-119416

(51) Int. Cl.
*C07D 515/00*    (2006.01)
*C07D 413/10*    (2006.01)
*C07D 409/10*    (2006.01)

(52) U.S. Cl.
CPC ............ *C07D 413/10* (2013.01); *C07D 409/10* (2013.01)
USPC ............ 549/52; 546/184; 546/202; 544/106; 544/146; 548/300.1; 548/525; 514/218; 514/233.5; 514/324; 514/422

(58) Field of Classification Search
CPC .. C07D 515/00; C07D 413/10; C07D 409/10; C07D 33/66
USPC ........... 549/52; 546/184; 544/106; 548/300.1
See application file for complete search history.

(56) References Cited

U.S. PATENT DOCUMENTS

| 2004/0116405 A1 | 6/2004 | Cox et al. |
| 2006/0183785 A1 | 8/2006 | Chakravarty et al. |
| 2009/0069305 A1 | 3/2009 | Gaul et al. |
| 2011/0300152 A1 | 12/2011 | Li et al. |

FOREIGN PATENT DOCUMENTS

| JP | 2004-532188 A | 10/2004 |
| JP | 2006-522130 A | 9/2006 |
| JP | 2012-508010 A | 4/2012 |
| WO | WO 03/004458 | * 1/2003 ............ C07C 233/81 |
| WO | WO 2005/009993 A1 | 2/2005 |
| WO | WO 2013-072694 A1 | 5/2013 |

OTHER PUBLICATIONS

Heike Wulff, et al, "Modulators of Small-and Intermediate-Conductance Calcium-Activated Potassium Channels and their Therapeutic Indications", Current Medicinal Chemistry, 2007, vol. 14, p. 1437-1457.

Damian McHugh, et al., "Effect of Small and Intermediate Conductance Potassium Channel Modulators on Visceral Hypersensitivity and Function", AHA Abstracts, T1386, Gastroenterology, 2008, vol. 134, Issue 4, Supp. 1, A-544.

Jesse LoVerme, et al., "Rapid Broad-Spectrum Analgesia through Activation of Peroxisome Proliferator-Activated Receptor-α", Journal of Pharmacology and Experimental Therapeutics, 2006, vol. 319, No. 3, pp. 1051-1061.

L.C. Mongan, et al., "The Distribution of Small and Intermediate Conductance Calcium-Activated Potassium Channels in the Rat Sensory Nervous System", Neuroscience 131 (2005) 161-175.

International Search Report and Written Opinion (with partial English translation) issued in PCT/JP2014/065141, Jun. 6, 2014, 15 pp.

* cited by examiner

*Primary Examiner* — Savitha Rao
*Assistant Examiner* — Angela Brown-Pettigrew
(74) *Attorney, Agent, or Firm* — Oblon, McClelland, Maier & Neustadt, L.L.P.

(57) ABSTRACT

The present invention is directed to compounds of Formula I:

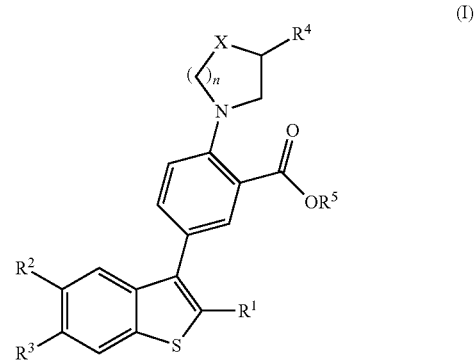

wherein $R^1$, $R^2$, $R^3$, $R^4$, $R^5$, X and n are described herein. These compounds and their pharmaceutically acceptable salts thereof are useful as IK1 channel activators.

14 Claims, No Drawings

BENZOTHIOPHENE COMPOUND

TECHNICAL FIELD

The present invention relates to a benzothiophene compound useful as an active ingredient of a pharmaceutical composition, in particular, a pharmaceutical composition for treating visceral pain, inflammatory pain, osteoarthritis pain, neuropathic pain, or fibromyalgia. In addition, the invention relates to an agent for preventing and/or treating inflammatory pain, osteoarthritis pain, neuropathic pain, or fibromyalgia comprising an intermediate conductance calcium-activated potassium channel activator (hereinafter referred to as an IK1 channel activator).

BACKGROUND ART

A potassium channel activated by calcium is expressed in various animal cells, and plays an important role in the regulation of cell functions. That is, the potassium channel activated by calcium performs potassium excretion by opening the channel in response to an increase in intracellular calcium in excitable and non-excitable cells, and regulates membrane potentials by inducing after-hyperpolarization. The potassium channel activated by calcium is classified as a large conductance channel (BK), a small conductance channel (SK), and an intermediate conductance channel (IK). In these channels, it was confirmed that the IK channel is expressed in lymphocytes, red blood cells, fibroblasts, vascular endothelial cells, airway epitheliums, an gastrointestinal tract, peripheral nerves, dorsal root ganglions, and the like and it was suggested that the IK channel is involved in diseases which target these (Current Medicinal Chemistry, 2007, vol. 14, p. 1437-1457). In addition, from the fact that it was reported that the IK1/SK dual opener improves visceral hypersensitivity and abnormal bowel movement (Gastroenterology, 2008, vol. 134, Issue 4, Supplement 1, p. A-544, T1386), a possibility of treatment for irritable bowel syndrome (IBS) was suggested.

On the other hand, there is a report that the IK1 channel is expressed in the sensory nervous system, but there is no change in the expression level in a neuropathic pain model and an inflammatory pain model (Neuroscience, 2005, vol. 131, p. 161-175) and a report that the IK1 is involved in the analgesic action of a PPAR agonist (The Journal of Pharmacology and Experimental Therapeutics, 2006. vol. 319, p. 1051-1061). However, a certain view has not been obtained for the relationship between the IK1 channel and a pain disorder. Furthermore, there has been no report showing that the IK1 channel activator is effective in inflammatory pain, osteoarthritis pain, neuropathic pain, or fibromyalgia, using disease animal models.

DISCLOSURE OF INVENTION

Problems to be Solved by the Invention

The invention provides a novel compound which is useful as an active ingredient of a drug, in particular, a pharmaceutical composition for preventing and/or treating visceral pain, inflammatory pain, osteoarthritis pain, neuropathic pain, or fibromyalgia.

In addition, the invention relates to an agent for preventing or treating inflammatory pain, osteoarthritis pain, neuropathic pain, or fibromyalgia comprising an IK1 channel activator.

Means for Solving the Problems

The present inventors have conducted intensive studies on IK1 channel activators, and as a result, they have found that the benzothiophene compound of the invention has excellent effects, thereby completing the invention.

That is, the present invention relates to a compound of the formula (I) or a salt thereof, and a pharmaceutical composition comprising a compound of the formula (I) or a salt thereof and a pharmaceutically acceptable excipient.

[Chem. 1]

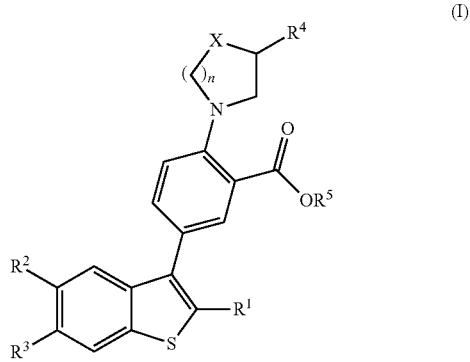

(In the formula,
X is —O—, —CH$_2$—, —NH—, or —N(lower alkyl)-,
n is an integer of 1 to 3,
R$^1$ is —H, halogen, or lower alkyl,
R$^2$ and R$^3$ are each the same as or different from each other, and are —H, halogen, lower alkyl, or halo-lower alkyl,
R$^4$ is —H or -Lk-NH—R$^0$,
Lk is lower alkylene or a bond,
R$^0$ is lower alkyl, -lower alkylene-OH, or cycloalkyl,
provided that in a case where R$^4$ is —H, X is —N(lower alkyl)-, and
R$^5$ is —H or lower alkyl.)

In addition, unless otherwise specified, when symbols in a certain chemical formula in the present specification are also used in another chemical formula, the same symbol represents the same meaning.

Further, it has been found by pharmacological tests using disease animal models that an IK1 channel activator is effective to inflammatory pain, osteoarthritis pain neuropathic pain, or fibromyalgia, thereby completing the invention.

That is, the present invention relates to an agent for preventing and/or treating inflammatory pain, osteoarthritis pain neuropathic pain, or fibromyalgia comprising an IK1 channel activator as an active ingredient.

Further, the present invention relates to a pharmaceutical composition for treating visceral pain, inflammatory pain, osteoarthritis pain, neuropathic pain, or fibromyalgia comprising a compound of the formula (I) or a salt thereof.

Meanwhile, the pharmaceutical composition includes an agent for treating visceral pain, inflammatory pain, osteoarthritis pain, neuropathic pain, or fibromyalgia comprising a compound of the formula (I) or a salt thereof.

Furthermore, the present invention relates to:
(1) use of a compound of the formula (I) or a salt thereof for the manufacture of a pharmaceutical composition for treating visceral pain, inflammatory pain, osteoarthritis pain, neuropathic pain, or fibromyalgia;
(2) use of a compound of the formula (I) or a salt thereof for treating visceral pain, inflammatory pain, osteoarthritis pain, neuropathic pain, or fibromyalgia;
(3) a compound of the formula (I) or a salt thereof for treating visceral pain, inflammatory pain, osteoarthritis pain, neuropathic pain, or fibromyalgia; and (4) a method for treating visceral pain, inflammatory pain, osteoarthritis pain, neuropathic pain, or fibromyalgia comprising administering an effective amount of a compound of the formula (I) or a salt thereof to a subject.

Meanwhile, the term "subject" is a human being or another animal in need of prevention or treatment thereof, and according to a certain embodiment, a human being in need of prevention or treatment thereof.

Effects of the Invention

A compound of the formula (I) or the salt thereof has an IK1 channel activation effect, and can be used as an agent for preventing and/or treating visceral pain, inflammatory pain, osteoarthritis pain, neuropathic pain, or fibromyalgia.

In addition, the IK1 channel activator can also be used as an agent for preventing and/or treating inflammatory pain, osteoarthritis pain, neuropathic pain, or fibromyalgia.

EMBODIMENTS FOR CARRYING OUT THE INVENTION

Hereinafter, the invention will be described in detail.
In the present specification, the "lower alkyl" is linear or branched alkyl having 1 to 6 carbon atoms (also referred to as $C_{1-6}$ alkyl; the number of carbon is hereinafter referred in the same manner), and examples thereof include methyl, ethyl, n-propyl, isopropyl, n-butyl, isobutyl, sec-butyl, tert-butyl, n-pentyl, n-hexyl, and the like. In another embodiment, the lower alkyl is $C_{1-4}$ alkyl, in a further embodiment, the lower alkyl is methyl, ethyl, n-propyl, or tert-butyl, in a still further embodiment, the lower alkyl is methyl, in a still further embodiment, the lower alkyl is linear or branched alkyl having 4 carbon atoms ($C_4$ alkyl), and in a still further embodiment, the lower alkyl is tert-butyl.

In the specification, the "halo-lower alkyl" is lower alkyl substituted with 1 to 5 halogen atoms. In another embodiment, the halo-lower alkyl is lower alkyl substituted with 1 to 3 halogen atoms, and in a further embodiment, the halo-lower alkyl is —$CF_3$.

In the specification, the "lower alkylene" is a linear or branched $C_{1-6}$ alkylene, and examples thereof include methylene, ethylene, trimethylene, tetramethylene, pentamethylene, hexamethylene, propylene, methyl methylene, ethyl ethylene, 1,2-dimethyl ethylene, 1,1,2,2-tetramethyl ethylene, and the like. In another embodiment, the lower alkylene is $C_{1-4}$ alkylene, in a further embodiment, the lower alkylene is $C_4$ alkylene, and in a still further embodiment, the lower alkylene is methylene.

In the specification, "halogen" means F, Cl, Br, or I.

In the specification, the "cycloalkyl" is a saturated hydrocarbon ring group having 3 to 10 carbon atoms ($C_{3-10}$), and may have a bridge. Examples thereof include cyclopropyl, cyclobutyl, cyclopentyl, cyclohexyl, cycloheptyl, cyclooctyl, adamantyl, and the like. In another embodiment, the cycloalkyl is cycloalkyl having 3 to 8 carbon atoms ($C_{3-8}$ cycloalkyl), and in a further embodiment, the cycloalkyl is cyclobutyl.

Embodiments of the invention are shown below.
(1) A compound of the formula (I) and a salt thereof, in which $R^1$ is —H, —F, or —$CH_3$, in another embodiment, $R^1$ is —H or lower alkyl, in a further embodiment, $R^1$ is —H or —$CH_3$, in a still further embodiment, $R^1$ is —H, in a still further embodiment, $R^1$ is halogen, in a still further embodiment, $R^1$ is —F, in a still further embodiment, $R^1$ is lower alkyl, and in a still further embodiment, $R^1$ is —$CH_3$.

(2) A compound of the formula (I) and a salt thereof, in which $R^2$ is —H or halogen, in another embodiment, $R^2$ is —H, —F, or —Cl, in a further embodiment, $R^2$ is —H, in a still further embodiment, $R^2$ is halogen, and in a still further embodiment, $R^2$ is —F or —Cl.

(3) A compound of the formula (I) and a salt thereof, in which $R^3$ is halogen or a halo-lower alkyl, in another embodiment, $R^3$ is —F, —Cl, or —$CF_3$, in a further embodiment, $R^3$ is halogen, in a still further embodiment, $R^3$ is —F or —Cl, in a still further embodiment, $R^3$ is —Cl, in a still further embodiment, $R^3$ is a halo-lower alkyl, and in a still further embodiment, $R^3$ is —$CF_3$.

(4) A compound of the formula (I) and a salt thereof, in which $R^4$ is -Lk-NH—$R^0$.

(5) A compound of the formula (I) and a salt thereof, in which Lk is lower alkylene, in another embodiment, Lk is $C_{1-4}$ alkylene, and in a further embodiment, Lk is —$CH_2$—.

(6) A compound of the formula (I) and a salt thereof, in which $R^0$ is $C_4$ alkyl, —$C_4$ alkylene-OH or $C_{3-8}$ cycloalkyl, in another embodiment, $R^0$ is $C_{3-8}$ cycloalkyl, in a further embodiment, $R^0$ is cyclobutyl, in a still further embodiment, $R^0$ is $C_4$ alkyl, and in a still further embodiment, $R^0$ is tert-butyl.

(7) A compound of the formula (I) and a salt thereof, in which $R^5$ is —H or —$CH_3$, and in another embodiment, $R^5$ is —H.

(8) A compound of the formula (I) and a salt thereof, in which X is —O— or —$CH_2$—, in another embodiment, X is —O—, and in a further embodiment, X is —$CH_2$—.

(9) A compound of the formula (I) and a salt thereof, in which n is 2.

(10) A compound of the formula (I) and a salt thereof, which is a combination of two or more of the embodiments as described in (1) to (9).

In addition, specific examples of the combination in (10) include the following embodiments.

(11) A compound of the formula (I) and a salt thereof, in which $R^1$ is lower alkyl, $R^2$ is —H, $R^3$ is halogen, $R^4$ is -Lk-NH—$R^0$, Lk is —$CH_2$—, $R^0$ is $C_{3-8}$ cycloalkyl, $R^5$ is —H, X is —O—, and n is 2.

(12) A compound of the formula (I) and a salt thereof, in which $R^1$ is —H, $R^2$ is a halogen, $R^3$ is a halo-lower alkyl, $R^4$ is -Lk-NH—$R^0$, Lk is —$CH_2$—, $R^0$ is $C_{3-8}$ cycloalkyl, $R^5$ is —H, X is —O—, and n is 2.

(13) A compound of the formula (I) and a salt thereof, in which $R^1$ is lower alkyl, $R^2$ is halogen, $R^3$ is halogen, $R^4$ is -Lk-NH—$R^0$, Lk is —$CH_2$—, $R^0$ is $C_{3-8}$ cycloalkyl, $R^5$ is —H, X is —O—, and n is 2.

In addition, examples of other specific embodiments of the combination in (10) include the following (a) to (f).
(a) A compound of the formula (I) and a salt thereof, in which $R^4$ is -Lk-NH—$R^0$.
(b) The compound of (a) and a salt thereof, in which X is —O— or —$CH_2$—.
(c) The compound of (b) and a salt thereof, in which n is 2.
(d) The compound of (c) and a salt thereof, in which Lk is —$CH_2$—.
(e) The compound of (d) and a salt thereof, in which $R^5$ is —H.
(f) The compound of (e) and a salt thereof, in which $R^0$ is $C_4$ alkyl, —$C_4$ alkylene-OH, or $C_{3-8}$ cycloalkyl.

Examples of embodiments of the specific compounds included in the invention include the following compounds and salts thereof:
5-(6-chloro-2-methyl-1-benzothiophen-3-yl)-2-{(2R)-2-[(cyclobutylamino)methyl]morpholin-4-yl}benzoic acid,
5-(6-chloro-2-fluoro-1-benzothiophen-3-yl)-2-{(2R)-2-[(cyclobutylamino)methyl]morpholin-4-yl}benzoic acid, 2-{(3R)-3-[(tert-butylamino)methyl)piperidin-1-yl}-5-[6-(trifluoromethyl)-1-benzothiophen-3-yl]benzoic acid,
5-[5-chloro-6-(trifluoromethyl)-1-benzothiophen-3-yl]-2-{(2R)-2-[(cyclobutylamino)methyl]morpholin-4-yl}benzoic acid, or
5-(6-chloro-5-(fluoro-2-methyl-1-benzothiophen-3-yl)-2-{(2R)-2-[(cyclobutylamino)methyl]morpholin-4-yl}benzoic acid.

Examples of other embodiments of the specific compounds included in the invention include the following compounds and salts thereof:
5-(6-chloro-2-methyl-1-benzothiophen-3-yl)-2-{(2R)-2-[(cyclobutylamino)methyl]morpholin-4-yl}benzoic acid hydrobromide,
5-(6-chloro-2-fluoro-1-benzothiophen-3-yl)-2-{(2R)-2-[(cyclobutylamino)methyl]morpholin-4-yl}benzoic acid hydrochloride,
2-{(3R)-3-[(tert-butylamino)methyl]piperidin-1-yl}-5-[6-(trifluoromethyl)-1-benzothiophen-3-yl]benzoic acid hydrochloride,
5-[5-chloro-6-(trifluoromethyl)-1-benzothiophen-3-yl]-2-{(2R)-2-[(cyclobutylamino)methyl]morpholin-4-yl}benzoic acid hydrochloride, or
5-(6-chloro-5-fluoro-2-methyl-1-benzothiophen-3-yl)-2-{(2R)-2-[(cyclobutylamino)methyl]morpholin-4-yl}benzoic acid hydrochloride.

The compounds of the formula (I) may be present as geometric isomers depending on the types of their substituents. In the present specification, even in the cases the compounds of formula (I) appear only in one isomer form, the invention encompasses other isomers and also encompasses separated isomers or mixtures thereof.

In addition, the compound of the formula (I) may have asymmetric carbon atoms or axial asymmetry, and optical isomers based thereon may be present. The invention also includes a separated optical isomer of the compound of the formula (I) or a mixture thereof.

Furthermore, the invention also encompasses a pharmaceutically acceptable prodrug of the compound represented by the formula (I). The pharmaceutically acceptable prodrug is a compound having a group which can be converted into an amino group, a hydroxyl group, a carboxyl group, or the like by solvolysis or under physiological conditions. As the group forming the prodrug, groups described in Prog. Med., 1985, vol. 5, p. 2157-2161, and "Pharmaceutical Research and Development, Drug Design" (Hirokawa Publishing Company), 1990, vol. 7, p. 163-198 can be exemplified.

In addition, the salts of the compound of the formula (I) is a pharmaceutically acceptable salt of the compound of the formula (I), and the compound of the formula (I) may form an acid addition salt or a salt with a base depending on the types of their substituents. Specific examples of the salt include the acid addition salts of inorganic acids such as hydrochloric acid, hydrobromic acid, hydroiodic acid, sulfuric acid, nitric acid, phosphoric acid, and the like, and organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methane sulfonic acid, ethane sulfonic acid, benzene sulfonic acid, p-toluene sulfonic acid, aspartic acid, glutamic acid, and the like, salts of inorganic bases such as sodium, potassium, magnesium, calcium, aluminum, and the like, and organic bases such as methylamine, ethylamine, ethanolamine, lysine, ornithine, and the like, salts of various amino acids such as acetylleucine, and the like and amino acid derivatives, ammonium salt, and the like.

Furthermore, the invention also encompasses various hydrates or solvates of the compound of the formula (I) or a salt thereof, and crystal polymorphism substances. In addition, the invention also encompasses compounds labeled with various radioactive or non-radioactive isotopes.

(Preparation Method)

The compound of the formula (I) and a salt thereof can be prepared by applying various known synthetic methods, using the characteristics based on the basic structure thereof or the types of substituents. At that time, it may be effective in a preparation technology that the functional group is substituted with a suitable protecting group (group which can be easily converted into the functional group) at the stage from a starting material to an intermediate depending on the types of functional groups. As such a protecting group, the protective groups described in "Greene's Protective Groups in Organic Synthesis (4th edition, 2006)" written by P. G. M. Wuts and T. W. Greene can be exemplified, and these may be suitably selected and used depending on the reaction conditions. In such a method, first, the protecting group is introduced, a reaction is carried out, and the protecting group is removed, if necessary. By doing this, it is possible to obtain a desired compound.

In addition, the prodrug of the compound of the formula (I) can be prepared by further carrying out a reaction by introducing a specific group at the stage from a starting material to an intermediate in the same manner as that of the above-described protecting group, or using the obtained compound of the formula (I). The reaction can be carried out by applying methods known to those skilled in the art such as general esterification, amidation, dehydration, or the like.

Hereinafter, representative preparation methods for the compound of the formula (I) will be described. Each of the preparation methods can also be carried out with reference to references described in the description. Moreover, the preparation method of the invention is not limited to examples described below.

[Chem. 2]

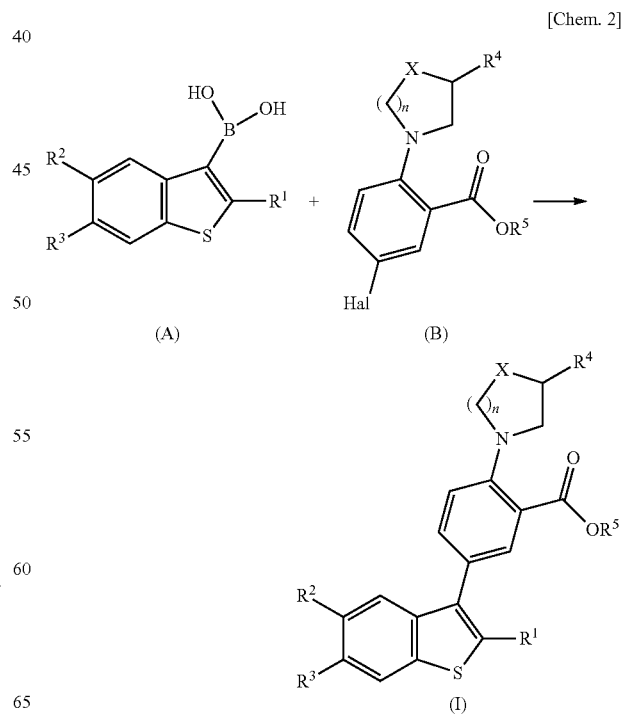

(In the formula, Hal represents Cl, Br, or I.)

The compound of the formula (I) includes (i) the compound of the formula (I), in which $R^5$ is lower alkyl (hereinafter referred to as a compound of the formula (I-1)), and (ii) the compound of the formula (I), in which $R^5$ is —H (hereinafter referred to as a compound of the formula (I-2)). Each general preparation method will be described below.

(i) The compound of the formula (I-1) can be prepared from compounds (A) and (B). The reaction is a so-called Suzuki coupling, in which the compound (1) is prepared by reacting a boronic acid compound (A) and the compound (B). The reaction can be carried out in the absence of a solvent, or a solvent which is inert to the reaction, such as aromatic hydrocarbons including toluene, xylene and the like, ethers including Et$_2$O, THF, DME, dioxane, and the like, halogenated hydrocarbons including DCM, DCE, chloroform, and the like, and aprotic solvents including DMF, DMSO, EtOAc, CH$_3$CN, and the like, and under heating to reflux from room temperature. The reaction is carried out in the presence of palladium, a phosphine ligand, and a metal base. As the palladium, Pd(PPh$_3$)$_4$, Pd(OAc)$_2$, Pd$_2$dba$_3$, and the like can be used. As the phosphine ligand, BINAP, DPPF, PPh$_3$, P(Bu$^t$)$_3$ and the like can be used. As the metal base, Na$_2$CO$_3$, K$_2$CO$_3$, Cs$_2$CO$_3$, NaOBu$^t$, K$_3$PO$_4$ and the like can be used.

(ii) The compound of the formula (I-2) can be prepared by dealkylating $R^5$ of the compound of the formula (I-1). For example, the dealkylation is a hydrolysis and the like. In a case of an alkaline hydrolysis, metal bases such as NaOH, KOH, Na$_2$CO$_3$, Cs$_2$CO$_3$, and the like can be used. In a case of an acid hydrolysis, hydrochloric acid and the like can be used. In both cases, the reaction temperature is from under ice-cooling to under a reflux condition, and it is possible to carry out the reaction under conditions in which a substrate is not decomposed. As a solvent, alcohols such as MeOH, EtOH, and the like, aprotic solvents such as DMF, DMSO, and the like, water or mixed solvents thereof can be used.

(Starting Material Synthesis 1)

[Chem. 3]

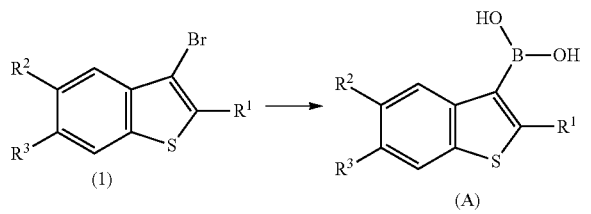

The starting compound (A) can be obtained by a reaction of a compound (1) and boric acid compounds such as triisopropylborate and the like.

In the reaction, the compound (1) and a boric acid compound such as triisopropylborate and the like are mixed in equivalent amounts, or either thereof in an excess amount, an organolithium reagent such as nBuLi and the like is added to the mixture under cooling preferably in a range from −78° C. to 0° C., and the resultant product is stirred in a solvent which is inert to the reaction or in the absence of a solvent usually at from a low temperature to room temperature, preferably 0° C. to 30° C., for 0.1 hours to 5 days. Examples of the solvent used herein include, but are not limited to, hydrocarbons such as hexane and the like, and ethers such as Et$_2$O, THF, and the like as long as the solvent does not interfere with the reaction.

(Starting Material Synthesis 2)

[Chem. 4]

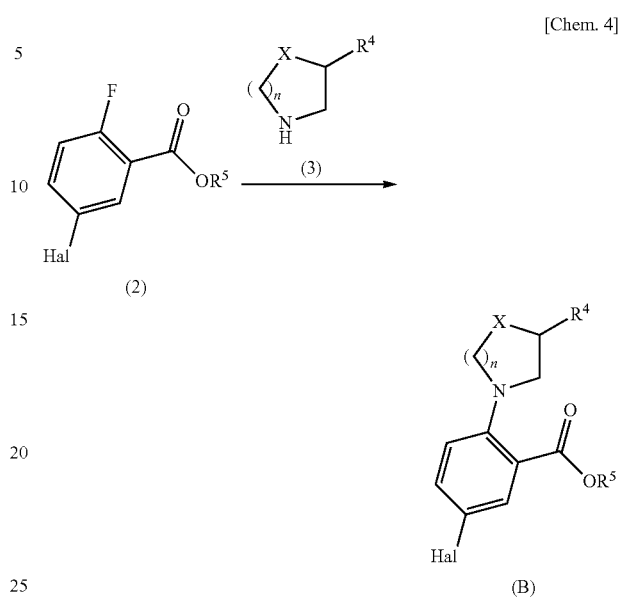

The starting compound (B) can be obtained by a reaction of a compound (2) and a compound (3).

In the reaction, the compound (2) and the compound (3) are mixed in equivalent amounts, or either thereof in an excess amount, and the mixture is stirred in a solvent which is inert to the reaction or in the absence of a solvent, usually for 0.1 hours to 5 days from cooling to heating to reflux, preferably 0° C. to 80° C. Examples of the solvent used herein include, but are not limited to, aromatic hydrocarbons, ethers, halogenated hydrocarbons, DMF, DMSO, EtOAc, CH$_3$CN, and mixed solvents thereof. When the reaction is carried out in the presence of an organic base such as TEA, DIPEA, and the like, or in the presence of an inorganic base such as K$_2$CO$_3$, Na$_2$CO$_3$, KOH, and the like, this case may be advantageous in terms of the smooth progress of the reaction.

REFERENCES

S. R. Sandler and W. Karo, "Organic Functional Group Preparations", 2nd edition, vol. 1, Academic Press Inc., 1991

"Courses in Experimental Chemistry" (5th edition) edited by The Chemical Society of Japan, vol. 14 (2005) (Maruzen Co., Ltd.)

(Starting Material Synthesis 3)

[Chem. 5]

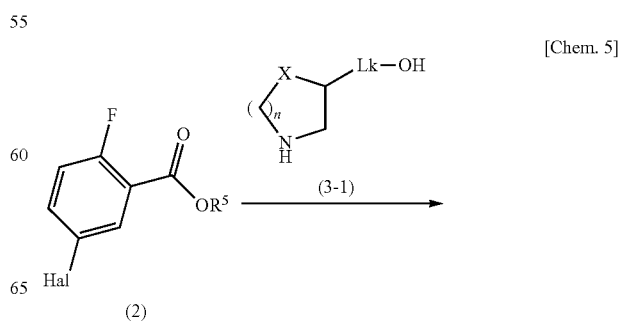

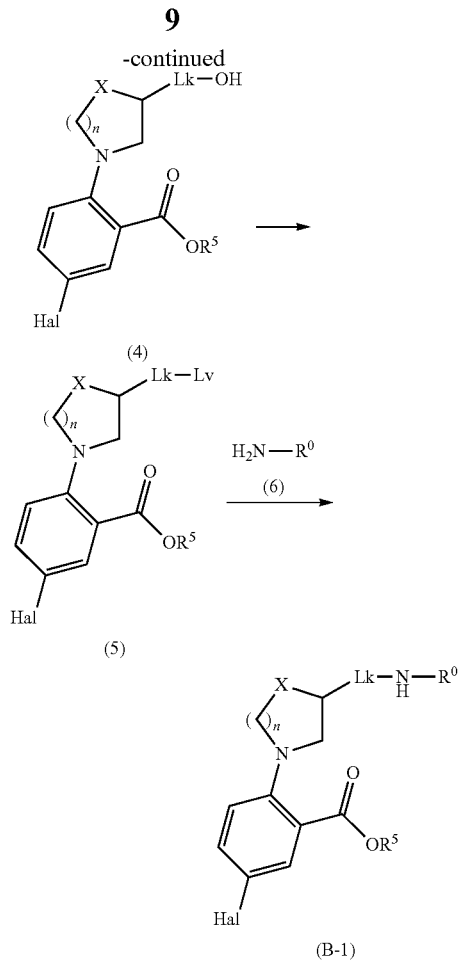

(In the formula, Lv represents halogen, —OMs, —OTs or the like.)

A compound (B-1) which is an embodiment of the starting compound (B) is obtained by converting a compound (4), which is obtained by reaction of the compound (2) and a compound (3-1), into a compound (5) and thereafter by reaction with a compound (6). The compound (4) is obtained from the compound (2) and the compound (3-1) in the same manner as described in the above-described Starting Material Synthesis 2. The compound (5) is obtained by converting a OH group of the compound (4) into a leaving group such as halogen, —OMs, —OTs, or the like using usual methods ("Courses in Experimental Chemistry" (5th edition) edited by The Chemical Society of Japan, vol. 14 (2005) (Maruzen Co., Ltd.)). In a final step, the compound (B-1) is obtained by reacting the compound (5) and the compound (6) using the same conditions as in the above-described Starting Material Synthesis 2.

The compound of the formula (I) is isolated and purified as a free compound, a salt thereof, a hydrate, a solvate, or a crystal polymorphism substance. The salt of the compound of the formula (I) can be prepared by a common salt formation reaction.

Isolation and purification are carried out by applying usual chemical operations such as extraction, fractional crystallization, various types of fractional chromatography, and the like.

Various isomers can be prepared by selecting a suitable starting compound, or can be separated using a difference in physicochemical properties among the isomers. For example, optical isomers are obtained by general optical resolution methods (for example, fractional crystallization leading to a diastereomeric salt with an optically active base or an acid, or chromatography using a chiral column or the like) of a racemic mixture, and can also be prepared from a suitable optically active starting compound.

The pharmacological activity of the compound of the formula (I) was confirmed by the following tests.

Moreover, in Test Examples 2 to 6, a 0.5% methyl cellulose suspension was used as a test drug.

Test Example 1

IK1 Channel Opening Activity Measurement Test

Cells ((1) T84 cells (which is known as IK1 channel expressing cells) or (2) human IK1 channel expressing cells (transgene: NM_002250.2, use cells: CHO dhfr−)) were seeded in a 384-well microplate so as to be 12000 cells/well. After incubation overnight, a medium was suctioned, and 20 μL of FLIPR Membrane Potential Assay Reagent (FLIPR Membrane Potential Assay kit, manufactured by Molecular Devices LLC) was added to the medium, followed by incubation at room temperature for 1 hour. Fluorescence intensity was measured at 530 nm/590 nm, which was set as a pre value. 20 μL of a buffer solution containing a test drug (which contains 0.01% pluronic acid and 20 mM Hepes-NaOH (pH7.4); 0.2% CHAPS in HBSS) was added, followed by incubation at room temperature for 1 hour, and a post value was measured. Activity of the test drug was determined from relative values where NS-309 (6,7-dichloro-1H-indole-2,3-dione 3-oxime, manufactured by Sigma-Aldrich Co., LLC; 0.2 μM; DMSO solution) treatment was set as 100%, and DMSO treatment was set as 0%. Activity value (%) at each concentration was plotted against a concentration of the test drug, and $EC_{50}$ value was calculated by a Logistic regression method.

The $EC_{50}$ values of an IK1 channel opening action of the several representative Example compounds of the invention are shown in the following Table (in the Table, No. means a number, and Ex means an Example compound number. The same shall apply hereinafter). Table 1 shows the results when using the T84 cells, and Table 2 shows the results when using the human IK1 channel expressing cells (transgene: NM_002250.2, use cells: CHO dhfr−). With P<0.05 in each assay, it was determined that there was a significant difference.

TABLE 1

| No. | $EC_{50}$ |
|---|---|
| Ex10 | 3.89 μM |
| Ex11 | 3.07 μM |
| Ex12 | 1.75 μM |
| Ex13 | 3.76 μM |
| Ex14 | 3.17 μM |
| Ex16 | 8.04 μM |
| Ex18 | 0.920 μM |
| Ex19 | 1.50 μM |

TABLE 2

| No. | $EC_{50}$ |
|---|---|
| Ex10 | 0.093 μM |
| Ex11 | 0.011 μM |
| Ex12 | 0.024 μM |
| Ex13 | 0.052 μM |

TABLE 2-continued

| No. | $EC_{50}$ |
|---|---|
| Ex14 | 0.028 µM |
| Ex16 | 0.033 µM |
| Ex18 | 0.048 µM |
| Ex19 | 0.0055 µM |

Test Example 2

Effect on Abdominal Pain by Rat Colorectal Distension

After Wistar male rats (CLEA Japan, Inc.) were anesthetized with isoflurane, a balloon was inserted into the colon. After awakening, the test drug was orally administered, and after 1 hour, abdominal pain induced by balloon expansion was measured as an indicator of an abdominal flexion behavior. Each stimulus (15, 30, 45, 60 mmHg) was repeatedly performed for 5 minutes at 5-minute intervals. A significant difference test of a solvent group and a test drug group was performed in comparison between groups using Student's t-test or Dunnett multiple comparison test. With $P<0.05$ in each assay, it was determined that there was a significant difference.

Effectiveness in the abdominal pain test by rat colorectal distension of the several representative Example compounds of the invention is shown in the following Table (In the Table, MED means a minimum effective dose. The same shall apply hereinafter). Each Example compound Ex10 or Ex18 exhibited significant activity in each dose shown in the following Table.

TABLE 3

| No. | MED |
|---|---|
| Ex10 | 0.3 mg/kg |
| Ex18 | 0.3 mg/kg |

Test Example 3

Inhibitory Effect on Hindlimb Weight Distribution in Adjuvant-Induced Arthritis Rat This model is a model to study inflammatory pain. 50 µL of killed *Mycobacterium tuberculosis* H37Ra (manufactured by DIFCO Laboratories) suspended in a liquid paraffin was subcutaneously administered into a right hindlimb footpad of a female Lewis rat (provided by Charles River Laboratories, Japan) so as to be 10 mg/mL. Next day, the solvent or the test drug was orally administered. After 1 or 2 hours, the weight distribution between the left and the right hindlimbs was measured using an Incapacitance Tester (manufactured by Linton Instrumentation). A significant difference test of a solvent group and a test drug group was performed in comparison between groups using Student's t-test or Dunnett multiple comparison test. With $P<0.05$ in each assay, it was determined that there was a significant difference.

Effectiveness in the adjuvant-induced arthritis rat test of the several representative Example compounds of the invention is shown in the following Table. Each Example compound Ex10, Ex11, Ex14 or Ex18 exhibited significant activity in each dose shown in the following Table.

TABLE 4

| No. | MED |
|---|---|
| Ex10 | 3 mg/kg |
| Ex11 | 3 mg/kg |
| Ex14 | 1 mg/kg |
| Ex18 | 3 mg/kg |

Test Example 4

Inhibitory Effect on Hindlimb Weight Distribution in Monoiodoacetate-Induced Osteoarthritis Model This model is a model of osteoarthritis, and action to osteoarthritis pain can be evaluated using the model. This test was performed based on The Journal of Pharmacology and Experimental Therapeutics, 2010, vol. 334, p. 955-963. Under isoflurane anesthesia, 1 mg/site of monoiodoacetate (hereinafter referred to as MIA) (manufactured by Sigma-Aldrich Co., LLC) solution was singly administered into the right knee joint cavity of male SD rats (provided by Charles River Laboratories, Japan). MIA was dissolved in physiological saline, and 50 µL thereof was administered using a 27 gauge×0.5 inches needle. 3 weeks after the MIA administration, the solvent or the test drug was orally administered. After 1 or 2 hours, the weight distribution between the left and the right hindlimb was measured using an Incapacitance Tester (manufactured by Linton Instrumentation). A significant difference test of a solvent group and a test drug group was performed in comparison between groups using Student's t-test or Dunnett multiple comparison test. With $P<0.05$ in each assay, it was determined that there was a significant difference.

Effectiveness with respect to a monoiodoacetate-induced osteoarthritis model of the several representative Example compounds of the invention is shown in the following Table. Each Example compound Ex10, Ex11, Ex14 or Ex18 exhibited significant activity in each dose shown in the following Table.

TABLE 5

| No. | Improvement rate |
|---|---|
| Ex10 | >50% (1 mg/kg) |
| Ex11 | >50% (1 mg/kg) |
| Ex14 | 42% (1 mg/kg) |
| Ex18 | >50% (1 mg/kg) |

Test Example 5

Effect on Tenderness Threshold Value in Reserpine-Induced Myalgia Model

This model is a model which imitates a fibromyalgia disease. This test was performed based on Pain, 2009, vol. 146, p 26-33. Reserpine (1 mg/kg) was subcutaneously administered into male SD rats (provided by Japan SLC, Inc, Japan) once a day for 3 days. After 5 days, the solvent or the test drug was orally administered. After 2 hours, a tenderness threshold value was measured using Randall-Selitto equipment (manufactured by Muromachi Kikai Co., Ltd.) in a gastrocnemius muscle. A significant difference test of a solvent group and a test drug-administered group was performed in comparison between groups using Student's t-test or Dunnett multiple comparison test. Here, a value obtained by administering the solvent to a normal rat to which reserpine was not administered was set as 100%, and a value of the reserpine group into which the solvent was administered was set as 0%. With P<0.05 in each assay, it was determined that there was a significant difference.

As a result, a representative Example compound 10 (Ex10) of the invention showed an improvement rate higher than 50% at a dose of 1 mg/kg. This result was significant activity.

Test Example 6

Action to Tenderness Threshold Value in Vagotomized Rat

It is reported that this model is a model which exhibits symptoms such as the fibromyalgia. The model was made based on Neuroscience, 2009, vol. 164, p. 1252-1262. Male SD rats (provided by Japan SLC, Inc, Japan) were anesthetized with somnopentyl, followed by shaving near a xiphisternum. Incision was performed along the midline from the xiphisternum to the tail side. A stomach and an esophagus under a diaphragm were exposed, and vagus nerves on both sides of the esophagus were transected. Muscle and skin were sutured in order. 1 to 3 weeks after the surgery, a decrease in the tenderness threshold value was confirmed. The solvent or the test drug was orally administered, and after 2 hours, the tenderness threshold value was measured using Randall-Selitto equipment (manufactured by Muromachi Kikai Co., Ltd.) in a gastrocnemius muscle. A significant difference test of a solvent group and a test drug group was performed in comparison between groups using Student's t-test or Dunnett multiple comparison test. With P<0.05 in each assay, it was determined that there was a significant difference.

Effectiveness of several representative Example compounds of the invention is shown in the following Table as an improvement rate when a value of a group in which the solvent was administered into a sham surgery group was set as 100%, and a value of a group in which the solvent was administered into a surgery group was set as 0%. Each Example compound Ex10, Ex14, Ex15 or Ex18 exhibited significant activity in each dose shown in the following Table.

TABLE 6

| No. | Improvement rate |
| --- | --- |
| Ex10 | >50% (3 mg/kg) |
| Ex14 | >50% (3 mg/kg) |
| Ex15 | >50% (3 mg/kg) |
| Ex18 | >50% (3 mg/kg) |

From the results of the above tests, it was confirmed that several compounds of the representative formula (I) or the salts thereof show the IK1 channel opening activity. Therefore, it was shown that the compounds of the invention have the IK1 channel opening activity, that is, the IK1 channel activation effect.

In addition, from the results of the above tests, it was found that the compound of the formula (I) or the salt thereof shows the effectiveness in terms of the effect on abdominal pain by rat colorectal distension, the inhibitory effect on the hindlimb weight distribution of the adjuvant-induced arthritis rat, the inhibitory effect on the hindlimb weight distribution in the monoiodoacetate-induced osteoarthritis model, the effect on the tenderness threshold value in the reserpine-induced myalgia model, and the tenderness threshold value in a vagotomized rat. Accordingly, the compound of the formula (I) or the salt thereof can be used in a prevention and/or a treatment for visceral pain, inflammatory pain, osteoarthritis pain, neuropathic pain, or fibromyalgia. Here, visceral pain, as certain embodiments, is an IBS symptom (abdominal pain). In addition, osteoarthritis pain is pain due to a osteoarthritis.

Furthermore, from the results of the above tests, it was found that the IK1 channel activator can also be used for prevention and/or treatment of inflammatory pain, osteoarthritis pain, neuropathic pain, or fibromyalgia.

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used. Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or EtOH. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include alcohols such as EtOH. Such a composition may further contain a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

In oral administration, the daily dose is generally from about 0.001 to 100 mg/kg, preferably from 0.01 to 30 mg/kg, and more preferably from 0.01 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing diseases for which the compound of the formula (I) is considered to be effective. In the combined use, co-administration or separate administration in succession may be performed, or administration may be performed at a desired time interval. The preparations to be co-administered may be a blend or may be prepared individually.

EXAMPLES

Hereinbelow, the preparation methods for the compound of the formula (I) will be described in more detail with reference to Examples. Further, the present invention is not limited to the compounds described in the Examples as described below. In addition, preparation methods of starting compounds are shown in Preparation Examples, and preparation methods of the compound of the formula (I) are shown in Examples. In addition, the preparation methods for the compound of the formula (I) are not limited to the preparation methods of the specific Examples as below, but the compound of the formula (I) can be prepared by any combination of the preparation methods or the methods that are apparent to a person skilled in the art.

In addition, the following abbreviations are used in Examples, Preparation Examples, Tables below, and the specification.
AIBN: 2,2'-azobisisobutyronitrile, brine: saturated brine, BINAP: 2,2'-bis(diphenylphosphino)-1,1'-binaphthyl, CHAPS: 3-[(3-cholamidopropyl)dimethylammonio]-1-propanesulfonate, DCE: dichloroethane, DCM: dichloromethane, DIPEA: diisopropylethylamine, DME: 1,2-dimethoxyethane, DMF: N,N-dimethylformamide, DMSO: dimethyl sulfoxide, DPPF: 1,1'-bis(diphenylphosphino)ferrocene, Et$_2$O: diethyl ether, EtOAc: ethyl acetate, EtOH: ethanol, HBSS: Hanks' balanced salt solution, Hepes: 4-(2-hydroxyethyl)-1-piperazine ethanesulfonic acid, Hepes-NaOH (pH 7.4): aqueous Hepes solution of which pH is adjusted to pH 7.4 with NaOH, KOBu$^t$: potassium tert-butoxide, MED: minimum effective dose, MeOH: methanol, MgSO$_4$: anhydrous magnesium sulfate, Na$_2$SO$_4$: Anhydrous sodium sulfate, NaOBu$^t$: sodium tert-butoxide, Pd(OAc)$_2$: palladium (II) acetate, Pd$_2$dba$_3$: tris(dibenzylideneacetone)dipalladium(0), Pd(PPh$_3$)$_4$: tetrakis(triphenylphosphine)palladium(0), P(Bu$^t$)$_3$: tri-tert-butylphosphine, PPh$_3$: triphenylphosphine, nBuLi: n-butyl lithium, TEA: triethylamine, THF: tetrahydrofuran, and silica gel column: silica gel column chromatography.

—OMs: methanesulfonyloxy, and —OTs: p-toluenesulfonyloxy.

No.: number, Pr: Preparation Example compound number, Ex: Example compound number, Ref: Examples or Preparation Examples which were referred to (For example, in a case where Ex10 is stated in the column of Ref of Ex15 in the following Table, it shows that Example compound 15 (Ex15) can be prepared in the same manner as described in the text examples of Example compound 10 (Ex10)), Dat: physicochemical data, Str: chemical structure formula, and Inf: information of optically activity and of the salt of the compound. (Chiral represents an optically active substance. In a case of not being particularly described with respect to the salt, it represents a free form. In addition, for example, in a case where HCl is described in Tables, it represents a monohydrochloride.)

NMR (CDCl$_3$): a chemical shift value δ of $^1$H-NMR measured in a CDCl$_3$ solvent, NMR (DMSO-d$_6$): a chemical shift value δ of $^1$H-NMR measured in a DMSO-d$_6$ solvent, and NMR (DMSO-d$_6$+D$_2$O): a chemical shift value δ of $^1$H-NMR measured by adding D$_2$O in DMSO-d$_6$.

EI: m/z values measured by EI-MS, ESI: m/z values measured by ESI-MS, APCI: m/z values measured by APCI-MS, and APCI/ESI: m/z values measured by APCI and the ESI at the same time. Moreover, in a case where there is + or − at the suffix of the ESI, + means a MS value measured in a positive ion mode, and − means a MS value measured in a negative ion mode.

In addition, for the sake of convenience, the concentration mol/L is expressed as M. For example, a 1 M aqueous NaOH solution means a 1 mol/L aqueous NaOH solution.

Powder X-ray diffraction was measured using RINT-TTR II manufactured by Rigaku Corporation under the following conditions, that is, tube: Cu, tube current: 300 mA, tube voltage: 50 kV, sampling width: 0.020°, scanning speed: 4°/min, wavelength: 1.54056 angstrom, and measuring diffraction angle range (2θ): 2.5° to 40°.

Each crystal is respectively characterized by a powder X-ray diffraction pattern and in the powder X-ray diffraction, crystal lattice distance or overall pattern is important in identification of the crystal due to the property of the data. Since the relative intensity can vary slightly depending on a direction of crystal growth, a particle size, or measurement conditions, it is not necessary to strictly interpret.

Preparation Example 1

A solution of nBuLi in hexane (1.59 M, 33.6 mL) was added dropwise to a mixture of 6-chloro-1-benzothiophene (6.00 g) and THF (180 mL) at −78° C., followed by stirring at −78° C. for 30 minutes. The temperature of the reaction mixture was increased to −40° C., followed by stirring for 5 minutes, and then iodomethane (10.1 g) was added thereto at −40° C. The temperature of the reaction mixture was increased to room temperature, followed by stirring for 12 hours. Water was added to the reaction mixture at room temperature, followed by extraction with EtOAc. The organic layer was washed with brine, dried over MgSO$_4$, and then concentrated under reduced pressure, thereby obtaining 6-chloro-2-methyl-1-benzothiophene (6.41 g).

Preparation Example 2

A mixture of 6-chloro-2-methyl-1-benzothiophene (6.40 g), chloroform (100 mL), and bromine (5.88 g) was stirred at room temperature for 18 hours, and then concentrated under reduced pressure. The residue was dissolved in EtOAc, and the organic layer was washed with water, a 10% aqueous Na$_2$S$_2$O$_3$ solution, and brine in this order. The organic layer was dried over Na$_2$SO$_4$ and concentrated under reduced pressure. The residue was purified by a silica gel column (dissolution medium: hexane), thereby obtaining 3-bromo-6-chloro-2-methyl-1-benzothiophene (8.50 g).

Preparation Example 3

A mixture of 6-(trifluoromethyl)-1-benzothiophene (1.57 g), acetic acid (8 mL), and N-bromosuccinimide (1.58 g) was stirred at 60° C. for 18 hours. The reaction mixture cooled to room temperature was diluted with chloroform. The organic layer was washed with a saturated aqueous Na$_2$S$_2$O$_3$ solution, a saturated aqueous Na$_2$CO$_3$ solution, water, and brine in this order, dried over MgSO$_4$, and then concentrated under reduced pressure. The residue was purified by a silica gel column (dissolution medium: hexane), thereby obtaining 3-bromo-6-(trifluoromethyl)-1-benzothiophene (1.94 g).

Preparation Example 4

A borane-dimethyl sulfide complex (12.4 mL) was added to a mixture of 6-chloro-5-fluoro-1-benzothiophen-2-carboxylic acid (10.0 g) and THF (100 mL) under ice-cooling, followed by stirring at room temperature for 30 minutes. Further, the reaction mixture was stirred at 50° C. for 4 hours, and dioxane (50 mL) was added thereto, followed by stirring at 80° C. for 2 hours. Water was added to the ice-cooled reaction mixture, followed by extraction with EtOAc. The organic layer was washed with brine, dried over MgSO$_4$, and concentrated under reduced pressure. The residue was purified by a silica gel column (dissolution medium: hexane/ EtOAc), thereby obtaining (6-chloro-5-fluoro-1-benzothiophen-2-yl)methanol (3.83 g).

Preparation Example 5

(6-Chloro-5-fluoro-1-benzothiophen-2-yl)methanol (5.94 g) was dissolved in DCM (59 mL), and thionyl chloride (4.89 g) was added thereto under ice-cooling, followed by stirring at room temperature for 2 hours. Thionyl chloride (1.63 g) was further added to the reaction mixture, followed by stirring at room temperature for 30 minutes. The reaction mixture was concentrated under reduced pressure. EtOAc was added to the residue, and the organic layer was washed with saturated aqueous sodium bicarbonate and brine in this order, dried over MgSO$_4$, and concentrated under reduced pressure. The residue was purified by a silica gel column (dissolution medium: hexane), thereby obtaining 6-chloro-2-(chloromethyl)-5-fluoro-1-benzothiophene (4.93 g).

Preparation Example 6

A mixture of 6-chloro-2-(chloromethyl)-5-fluoro-1-benzothiophene (4.93 g) and THF (47 mL) was added to a mixture of lithium aluminum hydride (1.19 g) and THF (30 mL) under ice-cooling, followed by stirring for 30 minutes under ice-cooling. The reaction mixture was stirred at room temperature for 2 hours, and water (1.2 mL), a 15% aqueous NaOH solution (1.2 mL), and water (3.6 mL) were added thereto under ice-cooling in this order, followed by stirring at room temperature for 30 minutes. The insoluble material was separated by filtration using celite, and the filtrate was concentrated under reduced pressure. The residue was purified by a silica gel column (dissolution medium: hexane), thereby obtaining 6-chloro-5-fluoro-2-methyl-1-benzothiophene (4.02 g).

Preparation Example 7

A mixture of 4-chloro-2,5-difluorobenzaldehyde (21.1 g), rhodanine (16.7 g), sodium acetate (39.2 g), and acetic acid (68 mL) was heated to reflux for 4 hours. Water (300 mL) was added to the reaction mixture cooled to room temperature, followed by stirring for 3 hours. The precipitate was collected by filtration, and dried under reduced pressure (34.1 g). A solution of NaOH (31.7 g) in water (284 mL) was added to the obtained product (34.1 g), followed by stirring at 80° C. for 3 hours. Concentrated hydrochloric acid (66 mL) was added to the reaction mixture cooled to room temperature, followed by stirring at room temperature for 30 minutes. The precipitate was collected by filtration (29.3 g). A mixture of the obtained product (29.3 g), DMSO (293 mL), and KOBu$^t$ (26.2 g) was stirred at 80° C. overnight. Saturated citric acid water (450 mL) was added to the reaction mixture cooled to room temperature, followed by stirring at room temperature for 30 minutes. The precipitate was collected by filtration, washed with water, and dried under reduced pressure, thereby obtaining 6-chloro-5-fluoro-1-benzothiophene-2-carboxylic acid (21.9 g).

Preparation Example 8

A mixture of 6-(trifluoromethyl)-1-benzothiophene-2-carboxylic acid (2.17 g), copper (0.25 g), and quinoline (8 mL) was stirred at 200° C. for 5 hours. The reaction mixture cooled to room temperature was diluted with EtOAc. The organic layer was washed with 1 M hydrochloric acid and brine in this order, dried over Na$_2$SO$_4$, and concentrated under reduced pressure. The residue was purified by a silica gel column (dissolution medium: hexane), thereby obtaining 6-(trifluoromethyl)-1-benzothiophene (1.62 g).

Preparation Example 9

A solution of nBuLi in hexane (2.76 M; 18.6 mL) was added dropwise to a mixture of 6-chloro-1-benzothiophene (7.20 g) and THF (216 mL) at −78° C., followed by stirring at −78° C. for 30 minutes. The temperature of the reaction mixture was increased to −40° C., followed by stirring for 5 minutes, and then N-fluorobenzenesulfonimide (21.5 g) was added thereto at −40° C. The temperature of the reaction mixture was increased to room temperature, followed by stirring for 12 hours. Water was added to the reaction mixture at room temperature, followed by extraction with EtOAc. The organic layer was washed with brine, dried over Na$_2$SO$_4$, and concentrated under reduced pressure. The residue was purified by a silica gel column (dissolution medium: hexane), thereby obtaining 6-chloro-2-fluoro-1-benzothiophene (3.12 g).

Preparation Example 10

A solution of nBuLi in hexane (1.59 M; 36.7 mL) was added dropwise to a mixture of 3-bromo-6-chloro-2-methyl- 1-benzothiophene (8.48 g), triisopropylborate (11.0 g), and THF (148 mL) at −78° C. under an argon atmosphere, followed by stirring at −78° C. for 30 minutes. After the temperature of the reaction mixture was increased to room temperature, the reaction mixture was stirred for 1 hour. 1 M hydrochloric acid was added thereto, followed by stirring at room temperature for 30 minutes and extracting with EtOAc. The organic layer was washed with brine, dried over $Na_2SO_4$, and concentrated under reduced pressure. Hexane was added to the residue, and the precipitate was collected by filtration. The filtered product was dried under reduced pressure, thereby obtaining (6-chloro-2-methyl-1-benzothiophen-3-yl)boronic acid (1.47 g).

Preparation Example 11

A solution of nBuLi in hexane (2.76 M; 9.1 mL) was added dropwise to a mixture of 6-chloro-2-fluoro-1-benzothiophene (3.11 g) and THF (62 mL) at −78° C. under an argon atmosphere. After the temperature of the reaction mixture was increased to −50° C. over 40 minutes, triisopropylborate (6.27 g) was added thereto, and the temperature was increased to room temperature, followed by stirring for 12 hours. 1 M hydrochloric acid was added to the reaction mixture at room temperature, followed by stirring for 15 minutes and extracting with EtOAc. The organic layer was washed with brine, dried over $Na_2SO_4$, and concentrated under reduced pressure. A mixed solvent of EtOAc and hexane was added to the residue, and the produced precipitate was collected by filtration. The product collected by filtration was dried under reduced pressure, thereby obtaining (6-chloro-2-fluoro-1-benzothiophen-3-yl)boronic acid (2.81 g).

Preparation Example 12

A solution of isopropyl magnesium chloride in THF (2.0 M; 27.2 mL) was added dropwise to a mixture of 1-bromo-2-chloro-5-fluoro-4-methylbenzene (8.10 g) and THF (55 mL) at −10° C. under an argon atmosphere, followed by stirring at −10° C. for 45 minutes. A mixture of iodine (18.4 g) and THF (26 mL) was added dropwise to the reaction mixture at −75° C., followed by stirring at −75° C. for 3 hours. A saturated aqueous $Na_2S_2O_3$ solution was added to the reaction mixture at −75° C., followed by stirring at room temperature for 15 minutes. Saturated aqueous sodium bicarbonate was added to the reaction mixture at room temperature, followed by extraction with EtOAc. The organic layer was washed with brine, dried over $Na_2SO_4$, and then concentrated under reduced pressure, thereby obtaining 1-chloro-4-fluoro-2-iodo-5-methylbenzene (9.71 g).

Preparation Example 13

Methyl difluoro(fluorosulfonyl)acetate (18.2 mL) and copper iodide (2.74 g) were added to a mixture of 1-chloro-4-fluoro-2-iodo-5-methylbenzene (9.71 g) and DMF (120 mL) at room temperature, followed by stirring at 95° C. for 3.5 hours under an argon atmosphere. EtOAc was added to the reaction mixture cooled to room temperature, followed by stirring, and the insoluble material was separated by filtration using celite filtration. Water was added to the filtrate, followed by extraction with EtOAc. The organic layer was washed with brine, dried over $Na_2SO_4$, and concentrated under reduced pressure. The residue was purified by a silica gel column (dissolution medium: hexane), thereby obtaining 1-chloro-4-fluoro-5-methyl-2-(trifluoromethyl)benzene (5.64 g).

Preparation Example 14

N-bromosuccinimide (5.19 g) and AIBN (218 mg) were added to a mixture of 1-chloro-4-fluoro-5-methyl-2-(trifluoromethyl)benzene (5.64 g) and carbon tetrachloride (85 mL) at room temperature, followed by stirring at 80° C. for 12 hours. After the reaction mixture was cooled to room temperature, N-bromosuccinimide (5.19 g) and AIBN (218 mg) were further added thereto, followed by stirring for 1 day at 80° C. Saturated aqueous sodium bicarbonate and a saturated aqueous $Na_2S_2O_3$ solution were added to the reaction mixture cooled to room temperature, and followed by extraction with chloroform. The organic layer was washed with brine, dried over $Na_2SO_4$, and concentrated under reduced pressure. The residue was purified by a silica gel column (dissolution medium: hexane), thereby obtaining 1-(bromomethyl)-5-chloro-2-fluoro-4-(trifluoromethyl)benzene (3.08 g).

Preparation Example 15

4-Methylmorpholine 4-oxide (2.47 g) was added to a mixture of 1-(bromomethyl)-5-chloro-2-fluoro-4-(trifluoromethyl)benzene (3.08 g) and acetonitrile (31 mL), followed by stirring for 1 hour in a water bath and further at room temperature for 1 hour. Saturated aqueous ammonium chloride was added to the reaction mixture under ice-cooling, followed by extraction with EtOAc. The organic layer was washed with brine, dried over $Na_2SO_4$, and concentrated under reduced pressure. The residue was purified by a silica gel column (dissolution medium: hexane/EtOAc), thereby obtaining 5-chloro-2-fluoro-4-(trifluoromethyl)benzaldehyde (1.32 g).

Preparation Example 16

A mixture of methyl 5-bromo-2-fluorobenzoate (5.00 g), (2S)-morpholin-2-yl methanol (3.39 g), DIPEA (4.16 g), and DMSO (25 mL) was stirred at 80° C. for 36 hours. Water was added to the reaction mixture cooled to room temperature, followed by extraction with a mixed solvent of EtOAc and $Et_2O$. The organic layer was washed with water and brine in this order, dried over $Na_2SO_4$, and concentrated under reduced pressure. The residue was purified by a silica gel column (dissolution medium: hexane/EtOAc), thereby obtaining methyl 5-bromo-2-[(2S)-2-(hydroxymethyl)morpholin-4-yl]benzoate (4.69 g).

Preparation Example 17

Methanesulfonyl chloride (2.35 g) was added to a mixture of methyl 5-bromo-2-[(2S)-2-(hydroxymethyl)morpholin-4-yl]benzoate (3.08 g), DCM (46 mL) and TEA (2.83 g) at room temperature, followed by stirring at room temperature for 2 hours. Saturated aqueous sodium bicarbonate was added to the reaction mixture at room temperature, followed by extraction with chloroform. The organic layer was washed with brine, dried over $Na_2SO_4$, and concentrated under reduced pressure. A mixture of the residue, DMSO (15 mL), and cyclobutylamine (6.63 g) was stirred at 60° C. for 18 hours. Water was added to the reaction mixture cooled to room temperature, followed by extraction with a mixed solvent of EtOAc and $Et_2O$. The organic layer was washed with water and brine in this order, dried over $Na_2SO_4$, and concentrated under reduced pressure. The residue was purified by a basic silica gel column (dissolution medium: hexane/EtOAc), thereby obtaining methyl 5-bromo-2-{(2R)-2-[(cyclobutylamino)methyl]morpholin-4-yl}benzoate (1.96 g).

Preparation Example 18

A mixture of tert-butyl (4-[4-bromo-2-(methoxycarbonyl)phenyl]-1,4-diazepane-1-carboxylate) (3.00 g), MeOH (10 mL), and a solution of hydrogen chloride in dioxane (4 M; 10 mL) was stirred at room temperature for 3 hours, and concentrated under reduced pressure. Saturated aqueous sodium bicarbonate was added to the residue, followed by extraction with EtOAc. The organic layer was dried over $Na_2SO_4$, and then concentrated under reduced pressure, thereby obtaining methyl 5-bromo-2-(1,4-diazepan-1-yl)benzoate (1.96 g).

Preparation Example 19

DCE (19 mL), acetic acid (364 mg), and sodium triacetoxyborohydride (1.93 g) were mixed with methyl 5-bromo-2-(1,4-diazepan-1-yl)benzoate (950 mg) in this order, acetaldehyde (401 mg) was added thereto, and then the reaction mixture was stirred at room temperature for 2 hours. Saturated aqueous sodium bicarbonate was added to the reaction mixture, followed by stirring vigorously for 10 minutes and extracting with chloroform. The organic layer was dried over $Na_2SO_4$ and concentrated under reduced pressure. The residue was purified by a basic silica gel column (dissolution medium: hexane/EtOAc), thereby obtaining methyl 5-bromo-2-(4-ethyl-1,4-diazepan-1-yl)benzoate (624 mg).

Preparation Example 21

A mixture of (6-chloro-5-fluoro-2-methyl-1-benzothiophen-3-yl)boronic acid (598 mg), methyl 5-bromo-2-[(2S)-2-(hydroxymethyl)morpholin-4-yl]benzoate (577 mg), Pd (PPh$_3$)$_4$ (202 mg), DME (11.5 mL), and a 2 M aqueous $Na_2CO_3$ solution (2.6 mL) was stirred at 80° C. for 5 hours under an argon atmosphere. The reaction mixture cooled to room temperature was extracted with a mixed solvent of EtOAc and Et$_2$O. The organic layer was washed with brine, and concentrated under reduced pressure. The residue was purified by a silica gel column (dissolution medium: hexane/EtOAc), thereby obtaining methyl 5-(6-chloro-5-fluoro-2-methyl-1-benzothiophen-3-yl)-2-[(2S)-2-(hydroxymethyl)morpholin-4-yl]benzoate (750 mg).

Preparation Example 21-1

A mixture of (6-chloro-2-methyl-1-benzothiophen-3-yl)boronic acid (2.40 g), methyl 5-bromo-2-[(2S)-2-(hydroxymethyl)morpholin-4-yl]benzoate (2.50 g), Pd (PPh$_3$)$_4$ (875 mg), DME (50 mL), and a 2 M aqueous $Na_2CO_3$ solution (11.4 mL) was stirred at 80° C. overnight under an argon atmosphere. After the reaction mixture cooled to room temperature was diluted with EtOAc, the insoluble material was removed by celite filtration, and the filtrate was concentrated under reduced pressure. The obtained residue was purified by a silica gel column (dissolution medium: hexane/EtOAc), thereby obtaining methyl 5-(6-chloro-2-methyl-1-benzothiophen-3-yl)-2-[(2S)-2-(hydroxymethyl)morpholin-4-yl]benzoate (3.18 g).

Preparation Example 22

Methanesulfonyl chloride (0.28 mL) was added to a mixture of methyl 5-(6-chloro-5-fluoro-2-methyl-1-benzothiophen-3-yl)-2-[(2S)-2-(hydroxymethyl)morpholin-4-yl]benzoate (740 mg), DCM (14.8 mL), and TEA (0.69 mL) under ice-cooling and an argon atmosphere, and the temperature was increased to room temperature, followed by stirring for 2 hours. Saturated aqueous sodium bicarbonate was added to the reaction mixture, followed by extraction with chloroform. The organic layer was washed with brine, dried over $Na_2SO_4$, and then concentrated under reduced pressure. The residue was purified by a silica gel column (dissolution medium: hexane/EtOAc), thereby obtaining methyl 5-(6-chloro-5-fluoro-2-methyl-1-benzothiophen-3-yl)-2-[(2S)-2-{[(methylsulfonyl)oxy]methyl}morpholin-4-yl]benzoate (791 mg).

Preparation Example 22-1

Methanesulfonyl chloride (1.86 g) was added to a mixture of methyl 5-(6-chloro-2-methyl-1-benzothiophen-3-yl)-2-[(2S)-2-(hydroxymethyl)morpholin-4-yl]benzoate (3.18 g), DCM (32 mL), and TEA (2.24 g) under ice-cooling, followed by stirring at the same temperature for 1.5 hours. Saturated aqueous sodium bicarbonate was added to the reaction mixture under ice-cooling, followed by extraction with chloroform. The organic layer was dried over $Na_2SO_4$, and then concentrated under reduced pressure, thereby obtaining methyl 5-(6-chloro-2-methyl-1-benzothiophen-3-yl)-2-[(2S)-2-{[(methyl sulfonyl)oxy]methyl}morpholin-4-yl]benzoate (3.58 g).

Example 1

A mixture of (6-chloro-2-methyl-1-benzothiophen-3-yl)boronic acid (1.02 g), methyl 5-bromo-2-{(2R)-2-[(cyclobutylamino)methyl]morpholin-4-yl}benzoate (898 mg), Pd(PPh$_3$)$_4$ (271 mg), DME (29 mL) and a 2 M aqueous $Na_2CO_3$ solution (4.7 mL) was stirred at 100° C. for 18 hours under an argon atmosphere. Water was added to the reaction mixture cooled to room temperature, followed by extraction with EtOAc. The organic layer was dried over MgSO$_4$, and concentrated under reduced pressure. The residue was purified by a basic silica gel column (dissolution medium: hexane/EtOAc), thereby obtaining methyl 5-(6-chloro-2-methyl-1-benzothiophen-3-yl)-2-{(2R)-2-[(cyclobutylamino)methyl]morpholin-4-yl}benzoate (970 mg).

Example 10

A mixture of methyl 5-(6-chloro-2-methyl-1-benzothiophen-3-yl)-2-{(2R)-2-[(cyclobutylamino)methyl]morpholin-4-yl}benzoate (950 mg), a 1 M aqueous NaOH solution (9.5 mL), and EtOH (10 mL) was stirred at 50° C. for 12 hours. The reaction mixture cooled to room temperature was neutralized with 1 M hydrochloric acid, and concentrated under reduced pressure. The residue was purified by a octadecyl silica gel column (dissolution medium: 0.001 M hydrochloric acid/dioxane). The eluted fraction was concentrated under reduced pressure and mixed with EtOH. 1 M hydrochloric acid (1.8 mL) was added thereto, and concentrated under reduced pressure. The residue was washed with EtOH, thereby obtaining 5-(6-chloro-2-methyl-1-benzothiophen-3-yl)-2-{(2R)-2-[(cyclobutylamino)methyl]morpholin-4-yl}benzoic acid monohydrochloride (830 mg).

Example 25

A mixture of methyl 5-(6-chloro-5-fluoro-2-methyl-1-benzothiophen-3-yl)-2-[(2S)-2-{[(methylsulfonyl)oxy]methyl}morpholin-4-yl]benzoate (1.00 g), DMSO (10 mL), and cyclobutylamine (1.35 g) was stirred at 60° C. for 12 hours, and further stirred at 80° C. for 12 hours. Water was added to the reaction mixture cooled to room temperature, followed by extraction with EtOAc. The organic layer was washed with brine, dried over Na$_2$SO$_4$, and concentrated under reduced pressure. The residue was purified by a basic silica gel column (dissolution medium: hexane/EtOAc), thereby obtaining methyl 5-(6-chloro-5-fluoro-2-methyl-1-benzothiophen-3-yl)-2-{(2R)-2-[(cyclobutylamino)methyl]morpholin-4-yl}benzoate (845 mg).

Example 30

Methanesulfonyl chloride (178 mg) was added to a mixture of methyl 5-(6-chloro-2-methyl-1-benzothiophen-3-yl)-2-[(3S)-3-(hydroxymethyl)piperidin-1-yl]benzoate (293 mg), DCM (5 mL), and TEA (207 mg) at room temperature, followed by stirring at room temperature for 1.5 hours. Saturated aqueous sodium bicarbonate was added to the reaction mixture at room temperature, followed by extraction with chloroform. The organic layer was washed with brine, dried over Na$_2$SO$_4$, and concentrated under reduced pressure. A mixture of the residue and DMSO (4 mL), and 1-amino-2-methyl-2-propanol (610 mg) was stirred at 60° C. for 18 hours, and further stirred at 80° C. for 6 hours. Water was added to the reaction mixture cooled to room temperature, followed by extraction with EtOAc. The organic layer was washed with water, and brine in this order, dried over Na$_2$SO$_4$, and concentrated under reduced pressure. The residue was purified by a basic silica gel column (dissolution medium: hexane/EtOAc), thereby obtaining methyl 5-(6-chloro-2-methyl-1-benzothiophen-3-yl)-2-[(3R)-3-{[(2-hydroxy-2-methylpropyl)amino]methyl}piperidin-1-yl]benzoate (114 mg).

Example 31

A mixture of methyl 5-(6-chloro-2-methyl-1-benzothiophen-3-yl)-2-{(2R)-2-[(cyclobutylamino)methyl]morpholin-4-yl}benzoate (2.05 g), a 1 M aqueous NaOH solution (6.0 mL), and MeOH (15 mL) was stirred at 50° C. for 19 hours under an argon atmosphere. 1 M hydrochloric acid (6.0 mL) was added to the reaction mixture cooled to room temperature, and concentrated under reduced pressure. The residue was purified by a silica gel column (dissolution medium: chloroform/MeOH). The purified product was mixed with dioxane/H$_2$O (40 mL/2 mL), and a 47% aqueous hydrobromic acid solution (0.70 mL) was added thereto, followed by stirring at 60° C. for 13 hours. The resultant product was cooled to room temperature, and the precipitate was collected by filtration, thereby obtaining 5-(6-chloro-2-methyl-1-benzothiophen-3-yl)-2-{(2R)-2-[(cyclobutylamino)methyl]morpholin-4-yl}benzoic acid monohydrobromide (1.65 g).

In the same manner as methods of the above-described Preparation Examples or Examples, compounds of Preparation Examples and Examples shown in the following tables were prepared.

TABLE 7

| No. | Str |
|---|---|
| Pr 1 | 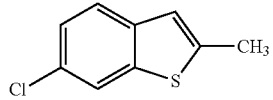 |
| Pr 1-1 | 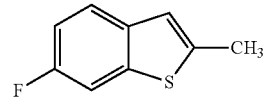 |
| Pr2 | 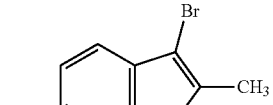 |
| Pr2-1 | 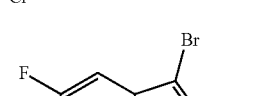 |
| Pr3 | 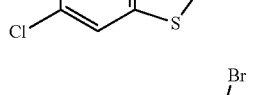 |
| Pr3-1 | 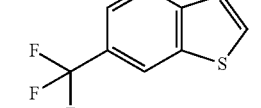 |
| Pr3-2 | 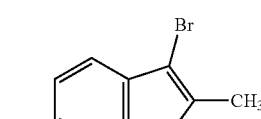 |
| Pr4 | 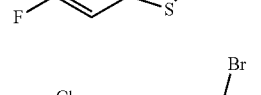 |

TABLE 8

| No. | Str |
|---|---|
| Pr5 | 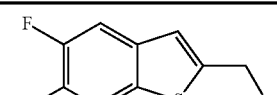 |
| Pr6 | 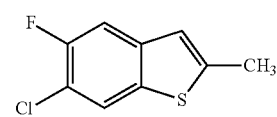 |

TABLE 8-continued

| No. | Str |
|---|---|
| Pr7 | 5-fluoro-6-chloro-benzothiophene-2-carboxylic acid |
| Pr7-1 | 5-chloro-6-trifluoromethyl-benzothiophene-2-carboxylic acid |
| Pr8 | 6-trifluoromethyl-benzothiophene |
| Pr8-1 | 5-chloro-6-trifluoromethyl-benzothiophene |
| Pr9 | 6-chloro-2-fluoro-benzothiophene |
| Pr10 | 6-chloro-2-methyl-benzothiophen-3-yl boronic acid |

TABLE 9

| No. | Str |
|---|---|
| Pr10-1 | 6-trifluoromethyl-benzothiophen-3-yl boronic acid |
| Pr10-2 | 6-fluoro-2-methyl-benzothiophen-3-yl boronic acid |

TABLE 9-continued

| No. | Str |
|---|---|
| Pr10-3 | 5-chloro-6-trifluoromethyl-benzothiophen-3-yl boronic acid |
| Pr10-4 | 5-fluoro-6-chloro-2-methyl-benzothiophen-3-yl boronic acid |
| Pr11 | 6-chloro-2-fluoro-benzothiophen-3-yl boronic acid |
| Pr12 | 2-chloro-4-fluoro-5-iodotoluene |
| Pr13 | 2-chloro-4-fluoro-5-trifluoromethyl-toluene |
| Pr14 | 2-chloro-4-trifluoromethyl-5-fluoro-benzyl bromide |

TABLE 10

| No. | Inf | Str |
|---|---|---|
| Pr15 | | 5-chloro-2-fluoro-4-trifluoromethyl-benzaldehyde |
| Pr16 | Chiral | methyl 5-bromo-2-[(2S)-2-(hydroxymethyl)morpholin-4-yl]benzoate |

TABLE 10-continued
| No. | Inf | Str |
|---|---|---|
| Pr16-1 | Chiral | 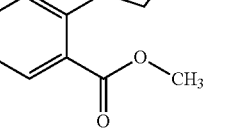 |
| Pr16-2 | Chiral | |
| Pr16-3 | | |
| Pr17 | Chiral | |
| Pr17-1 | Chiral | |
TABLE 11
| No. | Inf | Str |
|---|---|---|
| Pr18 | | |
TABLE 11-continued
| No. | Inf | Str |
|---|---|---|
| Pr18-1 | Chiral | |
| Pr19 | | |
| Pr19-1 | Chiral | |
| Pr20 | Chiral | |
| Pr20-1 | Chiral | 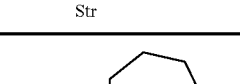 |

TABLE 12
| No. | Inf | Str |
|---|---|---|
| Pr21 | Chiral | 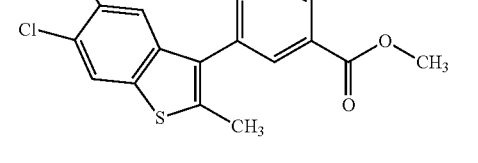 |
| Pr21-1 | Chiral | 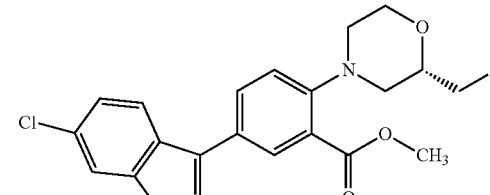 |
| Pr21-2 | Chiral | 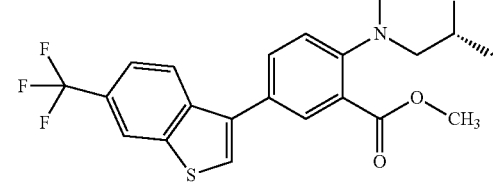 |
| Pr21-3 | Chiral | 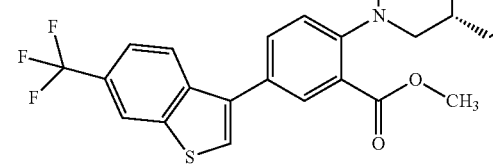 |
| Pr21-4 | Chiral | 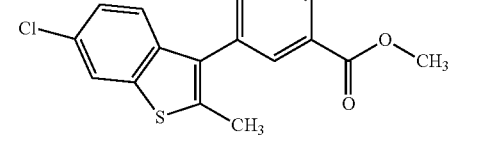 |
| Pr22 | Chiral | 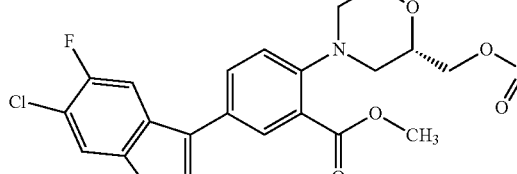 |

TABLE 13
| No. | Inf | Str |
|---|---|---|
| Pr22-1 | Chiral | |
| Pr22-2 | Chiral | |
| Pr22-3 | Chiral | |
| Pr22-4 | Chiral | |
TABLE 14
| No. | Inf | Str |
|---|---|---|
| Ex1 | Chiral | 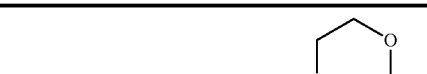 |

TABLE 15
| No. | Inf | Str |
|---|---|---|
| Ex2 | Chiral | 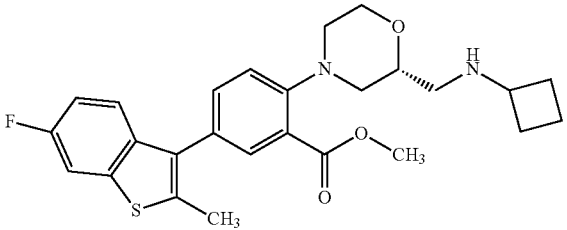 [SMILES: COC(=O)c1cc(-c2c(C)sc3cc(F)ccc23)ccc1N1CCO[C@H](CNC2CCC2)C1] |
| Ex3 | Chiral | 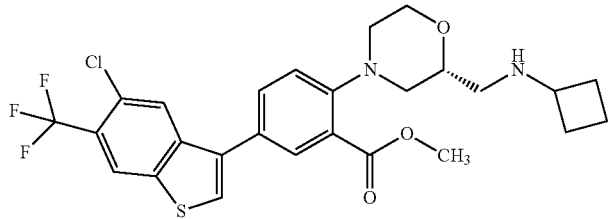 [SMILES: COC(=O)c1cc(-c2csc3cc(C(F)(F)F)c(Cl)cc23)ccc1N1CCO[C@H](CNC2CCC2)C1] |
| Ex4 | Chiral | 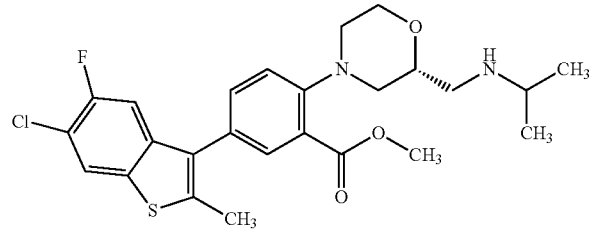 [SMILES: COC(=O)c1cc(-c2c(C)sc3cc(Cl)c(F)cc23)ccc1N1CCO[C@H](CNC(C)C)C1] |
| Ex5 | Chiral | 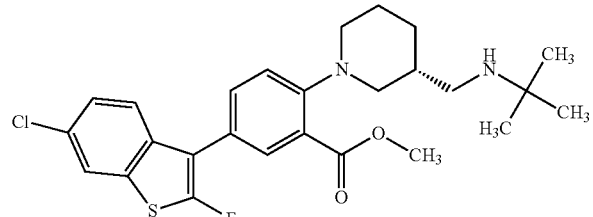 |
| Ex6 | Chiral | 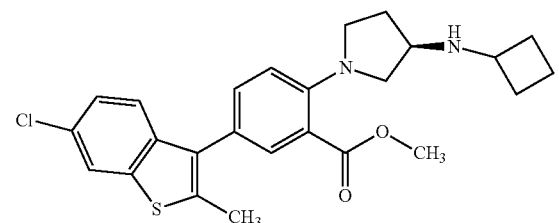 |
| Ex7 | Chiral | 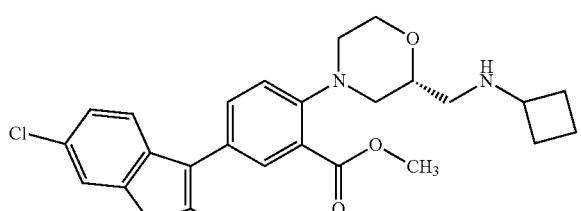 |

TABLE 16

| No. | Inf | Str |
|---|---|---|
| Ex8 | | |
| Ex9 | Chiral | |
| Ex10 | HCl Chiral | |
| Ex11 | HCl Chiral | |
| Ex12 | HCl Chiral | |
| Ex13 | HCl Chiral | |

TABLE 17

| No. | Inf | Str |
|---|---|---|
| Ex14 | HCl Chiral | |
| Ex15 | HCl Chiral | |
| Ex16 | HCl Chiral | |
| Ex17 | HCl Chiral | |
| Ex18 | HCl Chiral | |
| Ex19 | HCl Chiral | |

TABLE 18

| No. | Inf | Str |
|---|---|---|
| Ex20 | HCl Chiral | |
| Ex21 | HCl Chiral | |
| Ex22 | HCl Chiral | |
| Ex23 | HCl | |
| Ex24 | HCl Chiral | |
| Ex25 | Chiral | |

TABLE 19
| No. | Inf | Str |
|---|---|---|
| Ex26 | Chiral | 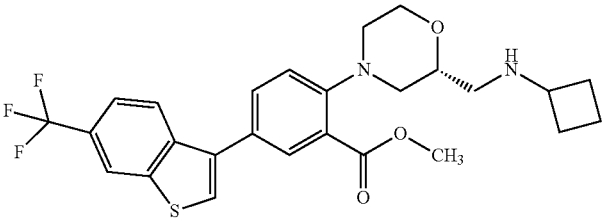 [SMILES: COC(=O)c1cc(-c2csc3cc(C(F)(F)F)ccc23)ccc1N1CCO[C@H](CNC2CCC2)C1] |
| Ex27 | Chiral | 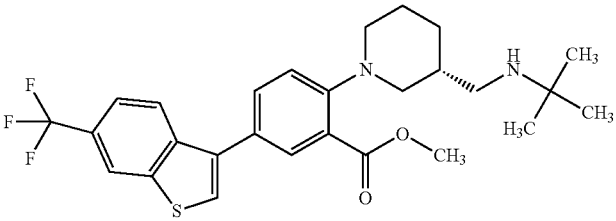 [SMILES: COC(=O)c1cc(-c2csc3cc(C(F)(F)F)ccc23)ccc1N1CCC[C@H](CNC(C)(C)C)C1] |
| Ex28 | Chiral | 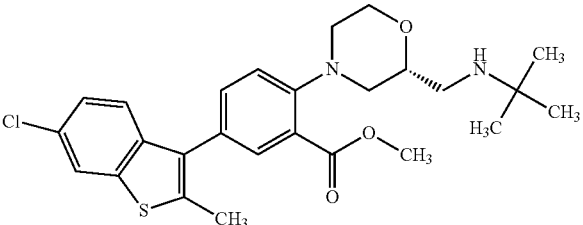 |
| Ex29 | Chiral | 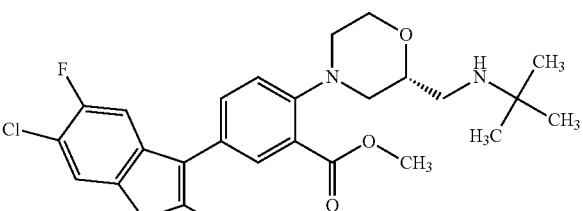 |
| Ex30 | Chiral | 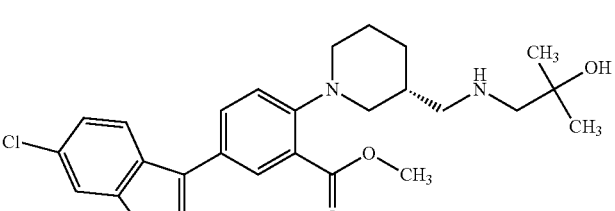 |
| Ex31 | HBr Chiral | 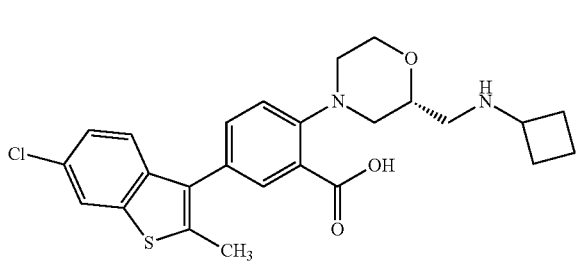 [SMILES: Cc1sc2cc(Cl)ccc2c1-c1ccc(N2CCO[C@H](CNC3CCC3)C2)c(C(=O)O)c1] |

TABLE 20

| No. | Ref | Dat |
|---|---|---|
| Pr1 | Pr1 | NMR (CDCl$_3$): 2.57 (3H, d, J = 1.2 Hz), 6.91-6.94 (1H, m), 7.25 (1H, dd, J = 2.0, 8.5 Hz), 7.54 (1H, d, J = 8.5 Hz), 7.71 (1H, d, J = 2.0 Hz) |
| Pr1-1 | Pr1 | NMR (CDCl$_3$): 2.55 (3H, s), 6.91 (1H, s), 7.03 (1H, dt, J = 2.4, 8.8 Hz), 7.41 (1H, dd, J = 2.2, 8.8 Hz), 7.55 (1H, dd, J = 5.1, 8.7 Hz) |
| Pr2 | Pr2 | NMR (CDCl$_3$): 2.53 (3H, s), 7.32-7.37 (1H, m), 7.56-7.62 (1H, m), 7.67-7.71 (1H, m) |
| Pr2-1 | Pr2 | NMR (CDCl$_3$): 2.55 (3H, s), 7.46 (1H, d, J = 9.3 Hz), 7.75 (1H, d, J = 6.4 Hz) |
| Pr3 | Pr3 | EI: 280, 282 |
| Pr3-1 | Pr3 | NMR (CDCl$_3$): 2.53 (3H, s), 7.15 (1H, dt, J = 2.4, 8.8 Hz), 7.42 (1H, dd, J = 2.4, 8.6 Hz), 7.64 (1H, dd, J = 5.0, 8.8 Hz) |
| Pr3-2 | Pr3 | EI: 314, 316 |
| Pr4 | Pr4 | NMR (CDCl$_3$): 1.92 (1H, t, J = 6.1 Hz), 4.92 (2H, dd, J = 0.8, 6.1 Hz), 7.13-7.17 (1H, m), 7.46 (1H, d, J = 9.4 Hz), 7.82 (1H, d, J = 6.6 Hz) |
| Pr5 | Pr5 | NMR (CDCl$_3$): 4.82 (2H, d, J = 0.8 Hz), 7.22-7.24 (1H, m), 7.47 (1H, d, J = 9.3 Hz), 7.81 (1H, d, J = 6.6 Hz) |
| Pr6 | Pr6 | NMR (CDCl$_3$): 2.57 (3H, d, J = 1.2 Hz), 6.90 (1H, brs), 7.37 (1H, d, J = 9.6 Hz), 7.72 (1H, d, J = 6.6 Hz) |
| Pr7 | Pr7 | ESI−: 229 |
| Pr7-1 | Pr7 | APCI/ESI−: 279 |
| Pr8 | Pr8 | EI: 202 |
| Pr8-1 | Pr8 | EI: 236 |
| Pr9 | Pr9 | NMR (CDCl$_3$): 6.67 (1H, d, J = 2.3 Hz), 7.31 (1H, dd, J = 1.9, 8.6 Hz), 7.52 (1H, d, J = 8.6 Hz), 7.61-7.65 (1H, m) |
| Pr10 | Pr10 | NMR (DMSO-d$_6$ + D$_2$O): 2.66 (3H, s), 7.34 (1H, dd, J = 2.0, 8.7 Hz), 7.91-7.97 (2H, m) |
| Pr10-1 | Pr10 | NMR (DMSO-d$_6$ + D$_2$O): 7.71 (1H, d, J = 8.5 Hz), 8.42 (1H, s), 8.46 (1H, s), 8.55 (1H, d, J = 8.5 Hz) |
| Pr10-2 | Pr10 | ESI−: 209 |
| Pr10-3 | Pr10 | APCI/ESI−: 279 |
| Pr10-4 | Pr10 | ESI−: 243 |

TABLE 21

| No. | Ref | Dat |
|---|---|---|
| Pr11 | Pr11 | NMR (DMSO-d$_6$ + D$_2$O): 7.37-7.49 (1H, m), 7.93-8.07 (2H, m) |
| Pr12 | Pr12 | EI: 270 |
| Pr13 | Pr13 | EI: 212 |
| Pr14 | Pr14 | EI: 290, 292 |
| Pr15 | Pr15 | EI: 226 |
| Pr16 | Pr16 | APCI/ESI+: 330, 332 |
| Pr16-1 | Pr16 | ESI+: 399, 401 |
| Pr16-2 | Pr16 | ESI+: 328, 330 |
| Pr16-3 | Pr16 | NMR (CDCl$_3$): 1.35-1.50 (9H, m), 1.84-2.00 (2H, m), 3.20-3.36 (4H, m), 3.41-3.63 (4H, m), 3.88 (3H, s), 6.89 (1H, d, J = 8.9 Hz), 7.36-7.43 (1H, m), 7.68 (1H, d, J = 2.6 Hz) |
| Pr17 | Pr17 | APCI/ESI+: 383, 385 |
| Pr17-1 | Pr17 | APCI/ESI+: 371, 373 |
| Pr18 | Pr18 | APCI/ESI+: 313, 315 |
| Pr18-1 | Pr18 | NMR (CDCl$_3$): 1.72-1.83 (1H, m), 2.11-2.21 (1H, m), 2.91 (1H, dd, J = 5.2, 9.9 Hz), 3.24-3.32 (1H, m), 3.34-3.43 (2H, m), 3.60-3.68 (1H, m), 3.88 (3H, s), 6.65 (1H, d, J = 9.0 Hz), 7.37 (1H, dd, J = 2.6, 9.0 Hz), 7.69 (1H, d, J = 2.6 Hz) |
| Pr19 | Pr19 | APCI/ESI+: 341, 343 |
| Pr19-1 | Pr19 | ESI+: 353, 355 |
| Pr20 | Ex25 | APCI/ESI+: 383, 385 |
| Pr20-1 | Ex25 | APCI/ESI+: 383, 385 |
| Pr21 | Pr21 | APCI/ESI+: 450 |
| Pr21-1 | Pr21-1 | APCI/ESI+: 432 |
| Pr21-2 | Pr21 | APCI/ESI+: 452 |
| Pr21-3 | Pr21 | APCI/ESI+: 450 |
| Pr21-4 | Pr21 | APCI/ESI+: 430 |
| Pr22 | Pr22 | APCI/ESI+: 528 |
| Pr22-1 | Pr22-1 | APCI/ESI+: 510 |
| Pr22-2 | Pr22 | ESI+: 406, 408 |
| Pr22-3 | Pr22 | APCI/ESI+: 530 |
| Pr22-4 | Pr22 | APCI/ESI+: 528 |

TABLE 22

| No. | Ref | Dat |
|---|---|---|
| Ex1 | Ex1 | APCI+: 485<br>NMR (DMSO-$d_6$): 1.50-1.69 (4H, m), 2.06-2.13 (2H, m),<br>2.40-2.48 (4H, m), 2.55-2.65 (2H, m), 2.85-2.93 (1H, m),<br>3.11-3.18 (2H, m), 3.25-3.32 (1H, m), 3.55-3.68 (2H, m), 3.82 (3H, s),<br>3.88-3.93 (1H, m), 7.23 (1H, d, J = 8.5 Hz),<br>7.36-7.38 (2H, m), 7.50 (1H, dd, J = 2.3, 8.5 Hz), 7.59 (1H, d, J = 2.3 Hz), 8.10 (1H, s)<br>NMR (CDCl$_3$): 1.59-1.79 (4H, m),<br>2.17-2.30 (2H, m), 2.46 (3H, s), 2.60 (1H, dd, J = 4.0, 12.2 Hz),<br>2.67-2.81 (2H, m), 3.00 (1H, dt, J = 3.1, 11.4 Hz), 3.17-3.32 (3H, m),<br>3.80-3.94 (5H, m),<br>3.97-4.04 (1H, m), 7.14 (1H, d, J = 8.4 Hz), 7.24 (1H, dd, J = 1.9, 8.6 Hz), 7.35 (1H, d, J = 8.6 Hz), 7.41 (1H, dd, J = 2.2, 8.4 Hz), 7.73 (1H, d, J = 2.2 Hz), 7.75 (1H, d, J = 1.9 Hz) |
| Ex2 | Ex1 | APCI+: 469<br>NMR (DMSO-$d_6$): 1.46-1.68 (4H, m), 2.04-2.15 (2H, m),<br>2.41-2.52 (4H, m), 2.56-2.66 (2H, m), 2.86-2.94 (1H, m),<br>3.11-3.18 (2H, m), 3.27-3.33 (1H, m), 3.56-3.69 (2H, m), 3.82 (3H, s),<br>3.88-3.94 (1H, m),<br>7.18-7.24 (2H, m), 7.38 (1H, dd, J = 5.2, 8.8 Hz), 7.50 (1H, dd, J = 2.1, 8.4 Hz),<br>7.59 (1H, d, J = 2.1 Hz), 7.87 (1H, dd, J = 2.4, 9.2 Hz) |
| Ex3 | Ex1 | APCI/ESI+: 539<br>NMR (CDCl$_3$): 1.59-1.79 (4H, m), 2.16-2.29 (2H, m),<br>2.56-2.82 (3H, m), 3.00 (1H, dt, J = 3.1, 11.3 Hz), 3.16-3.32 (3H, m),<br>3.77-3.95 (5H, m),<br>3.96-4.05 (1H, m), 7.16 (1H, d, J = 8.4 Hz), 7.58 (1H, dd, J = 2.2, 8.4 Hz), 7.60 (1H, s), 7.90 (1H, d, J = 2.2 Hz), 7.93 (1H, s), 8.24 (1H, s) |
| Ex4 | Ex1 | APCI+: 491 |
| Ex5 | Ex1 | APCI/ESI+: 489 |
| Ex6 | Ex1 | APCI/ESI+: 455 |
| Ex7 | Ex1 | APCI/ESI+: 489<br>NMR (CDCl$_3$): 1.57-1.79 (4H, m), 2.13-2.29 (2H, m),<br>2.53-2.80 (3H, m), 2.99 (1H, dt, J = 3.1, 11.4 Hz), 3.17-3.31 (3H, m),<br>3.79-3.94 (5H, m),<br>3.97-4.04 (1H, m), 7.14 (1H, d, J = 8.6 Hz), 7.34 (1H, dd, J = 2.0, 8.6 Hz),<br>7.54-7.59 (2H, m), 7.70 (1H, d, J = 2.0 Hz), 7.90 (1H, d, J = 2.2 Hz) |
| Ex8 | Ex1 | APCI/ESI+: 443 |

TABLE 23

| No. | Ref | Dat |
|---|---|---|
| Ex9 | Ex1 | APCI/ESI+: 489 |
| Ex10 | Ex10 | ESI+: 471<br>NMR (DMSO-$d_6$): 1.68-1.88 (2H, m),<br>2.11-2.35 (4H, m), 2.47 (3H, s), 2.85-3.15 (4H, m), 3.16-3.33 (2H, m),<br>3.64-3.84 (2H, m), 3.98-4.14 (2H, m),<br>7.35-7.43 (2H, m), 7.55 (1H, d, J = 8.4 Hz), 7.65 (1H, dd, J = 2.2, 8.4 Hz), 7.83 (1H, d, J = 2.2 Hz), 8.11-8.16 (1H, m), 9.10 (1H, brs), 9.33 (1H, brs) |
| Ex11 | Ex10 | APCI/ESI+: 475<br>NMR (DMSO-$d_6$): 1.68-1.88 (2H, m), 2.10-2.30 (4H, m),<br>2.80-3.14 (4H, m), 3.17-3.25 (1H, m), 3.25-3.40 (1H, m),<br>3.64-3.81 (2H, m), 3.94-4.12 (2H, m),<br>7.48-7.55 (2H, m), 7.63 (1H, d, J = 8.7 Hz), 7.77 (1H, dd, J = 2.1, 8.3 Hz), 7.96 (1H, d, J = 2.1 Hz), 8.22 (1H, d, J = 2.1 Hz), 9.03 (1H, brs), 9.20 (1H, brs) |
| Ex12 | Ex10 | APCI/ESI+: 491<br>NMR (DMSO-$d_6$): 1.67-1.88 (2H, m), 2.07-2.31 (4H, m),<br>2.86-3.14 (4H, m), 3.20 (1H, d, J = 11.7 Hz), 3.25-3.32 (1H, m),<br>3.64-3.82 (2H, m),<br>3.96-4.13 (2H, m), 7.56 (1H, d, J = 8.3 Hz), 7.78 (1H, d, J = 8.8 Hz),<br>7.83-7.89 (1H, m),<br>8.00-8.08 (2H, m), 8.19 (1H, s), 8.63 (1H, s), 9.11 (1H, brs), 9.40 (1H, brs) |
| Ex13 | Ex10 | ESI+: 455<br>NMR (DMSO-$d_6$): 1.69-1.86 (2H, m),<br>2.12-2.35 (4H, m), 2.46 (3H, s), 2.86-3.14 (4H, m), 3.17-3.24 (1H, m),<br>3.26-3.33 (1H, m), 3.65-3.80 (2H, m),<br>4.01-4.11 (2H, m), 7.23 (1H, dt, J = 2.5, 9.0 Hz), 7.39 (1H, dd, J = 5.2, 8.8 Hz),<br>7.56 (1H, d, J = 8.4 Hz), 7.65 (1H, dd, J = 2.1, 8.4 Hz), 7.83 (1H, d, J = 2.1 Hz),<br>7.89 (1H, dd, J = 2.4, 9.1 Hz), 9.20 (1H, brs), 9.52 (1H, brs) |
| Ex14 | Ex10 | APCI/ESI+: 491<br>NMR (DMSO-$d_6$): 1.21-1.41 (10H, m), 1.63-1.76 (1H, m),<br>1.90-2.03 (2H, m), 2.11-2.22 (1H, m), 2.82-2.99 (3H, m),<br>3.01-3.10 (1H, m), 3.13-3.21 (1H, m), 3.35-3.42 (1H, m), |

TABLE 23-continued

| No. | Ref | Dat |
|-----|-----|-----|
|     |     | 7.77-7.84 (2H, m), 7.95 (1H, dd, J = 2.2, 8.2 Hz), 8.02 (1H, d, J = 8.6 Hz), 8.21 (1H, d, J = 2.0 Hz), 8.24 (1H, s), 8.47 (1H, brs), 8.58-8.74 (2H, m) |

TABLE 24

| No. | Ref | Dat |
|-----|-----|-----|
| Ex15 | Ex10 | APCI/ESI+: 525<br>NMR (DMSO-$d_6$): 1.68-1.87 (2H, m), 2.11-2.30 (4H, m),<br>2.84-3.15 (4H, m), 3.16-3.34 (2H, m), 3.66-3.83 (2H, m),<br>3.97-4.13 (2H, m), 7.54 (1H, d, J = 8.5 Hz), 7.86 (1H, dd, J = 2.3, 8.5 Hz), 7.99 (1H, s), 8.02 (1H, d, J = 2.3 Hz), 8.28 (1H, s), 8.80 (1H, s), 9.07 (1H, brs), 9.28 (1H, brs) |
| Ex16 | Ex10 | APCI/ESI+: 473<br>NMR (DMSO-$d_6$): 1.31 (9H, s), 2.47 (3H, s), 2.87-3.04 (2H, m),<br>3.07-3.37 (4H, m), 3.72-3.82 (1H, m), 3.98-4.13 (2H, m),<br>7.34-7.42 (2H, m), 7.54 (1H, d, J = 8.3 Hz), 7.65 (1H, dd, J = 2.2, 8.3 Hz), 7.83 (1H, d, J = 2.2 Hz), 8.11-8.14 (1H, m), 8.54 (1H, brs), 8.80 (1H, brs) |
| Ex17 | Ex10 | ESI+: 477 |
| Ex18 | Ex10 | APCI/ESI+: 489<br>NMR (DMSO-$d_6$): 1.68-1.87 (2H, m),<br>2.11-2.35 (4H, m), 2.48 (3H, s), 2.84-3.15 (4H, m), 3.16-3.24 (1H, m),<br>3.25-3.34 (1H, m), 3.65-3.81 (2H, m),<br>3.99-4.11 (2H, m), 7.27 (1H, d, J = 10.2 Hz), 7.53 (1H, d, J = 8.3 Hz), 7.64 (1H, dd, J = 1.8, 8.3 Hz), 7.81 (1H, d, J = 1.8 Hz), 8.30 (1H, d, J = 6.9 Hz), 9.14 (1H, brs), 9.42 (1H, brs) |
| Ex19 | Ex10 | APCI/ESI+: 491<br>NMR (DMSO-$d_6$): 1.31 (9H, s), 2.48 (3H, s), 2.88-3.04 (2H, m),<br>3.06-3.27 (4H, m), 3.71-3.82 (1H, m),<br>3.99-4.14 (2H, m), 7.28 (1H, d, J = 10.2 Hz), 7.53 (1H, d, J = 8.3 Hz), 7.66 (1H, dd, J = 2.2, 8.3 Hz), 7.82 (1H, d, J = 2.2 Hz), 8.31 (1H, d, J = 7.0 Hz),<br>8.48-8.65 (1H, m), 8.89-9.03 (1H, m) |
| Ex20 | Ex10 | ESI+: 475 |
| Ex21 | Ex10 | ESI+: 441 |
| Ex22 | Ex10 | ESI+: 487 |
| Ex23 | Ex10 | APCI/ESI+: 429 |
| Ex24 | Ex10 | APCI/ESI+: 475 |

TABLE 25

| No. | Ref | Dat |
|-----|-----|-----|
| Ex25 | Ex25 | APCI/ESI+: 503<br>NMR (CDCl$_3$): 1.61-1.79 (4H, m),<br>2.17-2.28 (2H, m), 2.46 (3H, s), 2.60 (1H, dd, J = 4.1, 12.2 Hz),<br>2.68-2.81 (2H, m), 3.00 (1H, dt, J = 3.1, 11.5 Hz), 3.18-3.31 (3H, m),<br>3.80-3.93 (5H, m),<br>3.97-4.04 (1H, m), 7.14 (1H, d, J = 8.4 Hz), 7.17 (1H, d, J = 9.9 Hz), 7.38 (1H, dd, J = 2.2, 8.4 Hz), 7.71 (1H, d, J = 2.2 Hz), 7.77 (1H, d, J = 6.6 Hz) |
| Ex26 | Ex25 | APCI/ESI+: 505<br>NMR (CDCl$_3$): 1.59-1.81 (4H, m),<br>2.17-2.31 (2H, m), 2.61 (1H, dd, J = 4.0, 12.3 Hz),<br>2.68-2.81 (2H, m), 3.00 (1H, dt, J = 3.0, 11.4 Hz), 3.17-3.33 (3H, m),<br>3.80-3.95 (5H, m), 3.98-4.04 (1H, m), 7.15 (1H, d, J = 8.5 Hz), 7.55 (1H, s),<br>7.59-7.64 (2H, m), 7.91-8.00 (2H, m), 8.20 (1H, brs) |
| Ex27 | Ex25 | APCI/ESI+: 505<br>NMR (CDCl$_3$): 0.95-1.20 (10H, m), 1.68-1.95 (4H, m),<br>2.39-2.63 (3H, m), 2.76-2.87 (1H, m), 3.30-3.39 (1H, m),<br>3.43-3.55 (1H, m), 3.92 (3H, s), 7.14 (1H, d, J = 8.4 Hz), 7.53 (1H, s), 7.56 (1H, dd, J = 2.2, 8.4 Hz), 7.61 (1H, d, J = 1.4, 8.6), 7.86 (1H, d, J = 2.2 Hz), 7.96 (1H, d, J = 8.6 Hz),<br>8.17-8.20 (1H, m) |
| Ex28 | Ex25 | APCI/ESI+: 487<br>NMR (CDCl$_3$): 1.11 (9H, s), 2.45 (3H, s), 2.61 (1H, dd, J = 4.3, 11.5 Hz),<br>2.71-2.84 (2H, m), 3.02 (1H, dt, J = 3.1, 11.5 Hz), 3.17-3.25 (1H, m),<br>3.27-3.35 (1H, m), 3.78-3.93 (5H, m),<br>3.97-4.04 (1H, m), 7.14 (1H, d, J = 8.3 Hz), 7.24 (1H, d, J = 1.8, 8.6 Hz), 7.35 (1H, d, J = 8.6 Hz), 7.40 (1H, dd, J = 2.1, 8.3 Hz), 7.71 (1H, d, J = 2.1 Hz), 7.75 (1H, d, J = 1.8 Hz) |
| Ex29 | Ex14 | APCI/ESI+: 505<br>NMR (CDCl$_3$): 1.12 (9H, s), 2.46 (3H, s), 2.61 (1H, dd, J = 4.4, 11.5 Hz),<br>2.72-2.83 (2H, m), 3.02 (1H, dt, J = 3.1, 11.4 Hz), 3.17-3.25 (1H, m), |

TABLE 25-continued

| No. | Ref | Dat |
|---|---|---|
| | | 3.28-3.34 (1H, m), 3.78-3.94 (5H, m), 3.97-4.04 (1H, m), 7.14 (1H, d, J = 8.4 Hz), 7.18 (1H, d, J = 10.0 Hz), 7.39 (1H, dd, J = 2.3, 8.4 Hz), 7.69 (1H, d, J = 2.3 Hz), 7.77 (1H, d, J = 6.6 Hz) |
| Ex30 | Ex30 | APCI/ESI+: 501 |

TABLE 26

| No. | Ref | Dat |
|---|---|---|
| Ex31 | Ex31 | ESI+: 471<br>NMR (DMSO-$d_6$): 1.72-1.88 (2H, m), 2.07-2.26 (4H, m), 2.47 (3H, s), 2.83-3.16 (4H, m), 3.18-3.32 (2H, m), 3.68-3.82 (2H, m), 3.91-4.01 (1H, m), 4.04-4.14 (1H, m), 7.34-7.42 (2H, m), 7.54 (1H, d, J = 8.4 Hz), 7.65 (1H, dd, J = 2.2, 8.4 Hz), 7.83 (1H, d, J = 2.0 Hz), 8.14 (1H, dd, J = 0.6, 1.8 Hz), 8.72-8.94 (2H, m) 2Θ (°) = 8.3, 16.3, 16.9, 17.2, 24.0 |

INDUSTRIAL APPLICABILITY

A compound of the present invention has an IK1 channel activation effect, and can be used as an agent for preventing and/or treating visceral pain, inflammatory pain, osteoarthritis pain, neuropathic pain, or fibromyalgia.

In addition, according to the findings obtained in the present invention, an IK1 channel activator can also be used as an agent for preventing and/or treating inflammatory pain, osteoarthritis pain, neuropathic pain, or fibromyalgia.

The invention claimed is:

1. A compound of the following formula (I) or a salt thereof

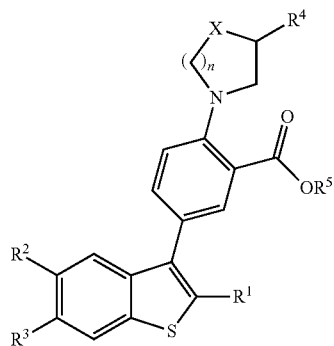

(I)

wherein
X is —O—, —CH$_2$—, —NH—, or —N(C$_1$-C$_6$ alkyl)-,
n is an integer of 1 to 3,
R$^1$ is —H, halogen, or lower alkyl,
R$^2$ and R$^3$ are each the same as or different from each other, and are —H, halogen, C$_1$-C$_6$ alkyl, or halo-C$_1$-C$_6$ alkyl,
R$^4$ is —H or -Lk-NH—R$^o$,
Lk is C$_1$-C$_6$ alkylene or a bond,
R$^o$ is C$_1$-C$_6$ alkyl, —C$_1$-C$_6$ alkylene-OH, or cycloalkyl, provided that in a case where R$^4$ is —H, X is —N(C$_1$-C$_6$ alkyl)-, and R$^5$ is —H or C$_1$-C$_6$ alkyl.

2. The compound or a salt thereof according to claim 1, wherein R$^4$ is -Lk-NH—R$^o$.

3. The compound or a salt thereof according to claim 2, wherein X is —O— or —CH$_2$—.

4. The compound or a salt thereof according to claim 3, wherein n is 2.

5. The compound or a salt thereof according to claim 4, wherein Lk is —CH$_2$—.

6. The compound or a salt thereof according to claim 5, wherein R$^5$ is —H.

7. The compound or a salt thereof according to claim 6, wherein R$^o$ is C$_4$ alkyl, —C$_4$ alkylene-OH, or C$_{3-8}$ cycloalkyl.

8. The compound or a salt thereof according to claim 1, wherein R$^1$ is C$_1$-C$_6$ alkyl, R$^2$ is —H, R$^3$ is halogen, R$^4$ is -Lk-NH—R$^o$, Lk is —CH$_2$—, R$^o$ is C$_{3-8}$ cycloalkyl, R$^5$ is —H, X is —O—, and n is 2.

9. The compound or a salt thereof according to claim 1, wherein R$^1$ is C$_1$-C$_6$ alkyl, R$^2$ is halogen, R$^3$ is halogen, R$^4$ is -Lk-NH—R$^o$, Lk is —CH$_2$—, R$^o$ is C$_{3-8}$ cycloalkyl, R$^5$ is —H, X is —O—, and n is 2.

10. The compound or a salt thereof according to claim 7, which is selected from the following group consisting of:
    5-(6-chloro-2-methyl-1-benzothiophen-3-yl)-2-{(2R)-2-[(cyclobutylamino)methyl]morpholin-4-yl}benzoic acid,
    5-(6-chloro-2-fluoro-1-benzothiophen-3-yl)-2-{(2R)-2-[(cyclobutylamino)methyl]morpholin-4-yl}benzoic acid,
    2-{(3R)-3-[(tert-butylamino)methyl]piperidin-1-yl}-5-[6-(trifluoromethyl)-1-benzothiophen-3-yl]benzoic acid,
    5-[5-chloro-6-(trifluoromethyl)-1-benzothiophen-3-yl]-2-{(2R)-2-[(cyclobutylamino)methyl]morpholin-4-yl}benzoic acid, and
    5-(6-chloro-5-(fluoro-2-methyl-1-benzothiophen-3-yl)-2-{(2R)-2-[(cyclobutylamino)methyl]morpholin-4-yl}benzoic acid.

11. The compound or a salt thereof according to claim 10, which is 5-(6-chloro-2-methyl-1-benzothiophen-3-yl)-2-{(2R)-2-[(cyclobutylamino)methyl]morpholin-4-yl}benzoic acid or a salt thereof.

12. The compound or a salt thereof according to claim 10, which is 5-(6-chloro-5-fluoro-2-methyl-1-benzothiophen-3-yl)-2-{(2R)-2-[(cyclobutylamino)methyl]morpholin-4-yl}benzoic acid or a salt thereof.

13. A pharmaceutical composition comprising the compound or a salt thereof according to claim 1 and a pharmaceutically acceptable excipient.

14. The pharmaceutical composition according to claim 13, which is an intermediate conductance calcium-activated potassium channel activator.

* * * * *